US010889798B2

(12) United States Patent
Jackson et al.

(10) Patent No.: US 10,889,798 B2
(45) Date of Patent: Jan. 12, 2021

(54) STABLE FUNGAL BLASTOSPORES AND METHODS FOR THEIR PRODUCTION, STABILIZATION AND USE

(71) Applicants: The United States of America, as Represented by the Secretary of Agriculture, Washington, DC (US); Embrapa, Santo Antonio de Goias (BR)

(72) Inventors: Mark A. Jackson, Peoria, IL (US); Gabriel Moura, Mascarin, Goiania (BR)

(73) Assignees: The United States of America, as represented by The Secretary of Agriculture, Washington, DC (US); EMPRES A BRASILIERA DE PESQUISA AGROPECUÁRIA

( * ) Notice: Subject to any disclaimer, the term of this patent is extended or adjusted under 35 U.S.C. 154(b) by 0 days.

(21) Appl. No.: 14/854,120

(22) Filed: Sep. 15, 2015

(65) Prior Publication Data

US 2016/0075992 A1    Mar. 17, 2016

Related U.S. Application Data

(60) Provisional application No. 62/050,473, filed on Sep. 15, 2014.

(51) Int. Cl.
*C12N 3/00* (2006.01)
*A01N 63/30* (2020.01)

(52) U.S. Cl.
CPC ............... *C12N 3/00* (2013.01); *A01N 63/30* (2020.01)

(58) Field of Classification Search
CPC .................................. A01N 63/04; C12N 3/00
See application file for complete search history.

(56) References Cited

U.S. PATENT DOCUMENTS

| 5,759,562 | A | 6/1998 | Rhodes et al. | |
|---|---|---|---|---|
| 5,968,808 | A | 10/1999 | Jackson | |
| 8,574,566 | B2 | 11/2013 | Prenerova et al. | |
| 2009/0074809 | A1* | 3/2009 | Jackson | A01G 1/04 424/195.15 |
| 2011/0280839 | A1* | 11/2011 | Ford | A01N 63/04 424/93.3 |
| 2016/0113289 | A1* | 4/2016 | Patel | A01N 63/04 424/93.5 |

OTHER PUBLICATIONS

Faria, M. et al., Application of Modified Atmosphere Packaging (Gas Flushing and Active Packaging) for Extending the Shelf Life of Beauveria Bassiana Conidia at High Temperatures, Biological Control, 2012, pp. 78-88, vol. 61.

Jackson, M.A. et al., Optimizing Nutritional Conditions for the Liquid Culture Production of Effective Fungal Biological Control Agents. J Ind Microbiol Biotechnol, Journal of Industrial Microbiology and Biotechnology, 1997, pp. 180-187, vol. 19.

Jackson, M.A. et al., Dissolved Oxygen Levels Affect Dimorphic Growth by the Entomopathogenic Fungus Isaria Fumosorosea, Biocontrol Science and Technology, 2012, pp. 67-79, vol. 22.

Lane, B.S. et al., Influence of Cultural Conditions on the Virulence of Conidia and Blastospores of Beauveria Bassiana to the Green Leafhopper, *Nephotettix viruescens*, Mycol. Res., 1991, pp. 829-833, vol. 95(7).

* cited by examiner

*Primary Examiner* — Robert J Yamasaki
(74) *Attorney, Agent, or Firm* — John D. Fado; Mark D. McNemar

(57) ABSTRACT

Described herein is a method for blastospore-based insect control products of entomopathogenic fungi including either *B. bassiana* or *I. fumosorosea* that produces high concentrations of stable, effective spores by identifying nutritional and environmental conditions required for the rapid production of high concentrations of a stable and infective yeast-like blastospore composition.

11 Claims, 12 Drawing Sheets
(7 of 12 Drawing Sheet(s) Filed in Color)

STABLE FUNGAL BLASTOSPORES AND METHODS FOR THEIR PRODUCTION, STABILIZATION AND USE

CROSS-REFERENCE

This application claims priority to U.S. Provisional Application No. 62/050,473, filed on Sep. 15, 2014.

BACKGROUND OF THE INVENTION

Field of Invention

The present invention pertains generally to methods and compositions related to the control of arthropod pests involving the use of entomopathogenic fungi. Specifically disclosed are methodologies and compositions for producing and drying desiccation-tolerant blastospores (vegetative cells) of *Beauveria bassiana* and *Isaria fumosorosea* for controlling soft-bodied insect pests.

Background

Plant disease and damage caused by arthropod pests results in significant economic losses to plant based agriculture and industries. Many and varied approaches have been pursued to control pests that attack plants, especially commercially valuable plants. Despite this, pest destruction of plants and plant products is still a major problem.

Traditionally, control of arthropod pests has been pursued through the application of chemical insecticides. The use of chemicals is subject to a number of disadvantages. The insect pests can and have developed tolerance to chemicals over time, producing resistant populations. Indeed, resistance to pesticides is a major challenge to the viability of chemical pest control in the agricultural and horticultural industries. Additionally, chemical pesticides are not always selective in their targets, often negatively impacting beneficial species, such as pollinators. Because of this and other adverse effects, such as effects on human health and the environment, other methods of biological control have long been investigated. One such approach is the use of certain entomopathogenic fungi as biological control agents. The revival of interest in biological control such as microbial insecticides over the last 20 years has come directly from public pressure in response to concerns about chemical toxicities. Biological control presents an alternative means of controlling arthropod pests which is potentially more effective and specific than current methods, as well as reducing dependence on chemicals.

Insect fungal pathogens are useful as biological control agents due to their ability to infect a wide range of insect pests and potential for mass-production. Production and formulation are key components to their success as commercial products. There are different methods for mass production, including solid substrate fermentation (SSF) for aerial conidia and liquid culture fermentation (LCF) for yeast-like blastospores, microcycle conidia, and microsclerotia. To date, the majority of the ascomycete fungal entomopathogens (Ascomycota: Hypocreales) deployed in inundative biocontrol strategies include *Beauveria bassiana* sensu lato (Bals.) Vuill., *B. brongniartii* (Sacc.) Petch, *Isaria fumosorosea* Wise (formerly *Paecilomyces fumosoroseus*), *Lecanicillium longisporum* and *L. muscarium* (Petch) R. Zare and W. Gams (formerly *Verticillium lecanii*), and *Metarhizium anisopliae* sensu lato (Metsch.) Sorokin., and aerial conidia comprise the main active ingredient of these mycoinsecticides that are mostly produced using solid culture techniques. Unfortunately, fermentation time for sporulation on solid substrates generally requires weeks and the process is labor-intensive with a high risk of contamination, resulting in high production costs. Liquid fermentation technology, on the other hand, can overcome these production hindrances/drawbacks and provide more economical scale-up capabilities to produce different fungal propagules under controlled nutritional and environmental conditions. Due to the short fermentation time of a few days, the ease of product recovery, the automation of the process, and the availability of inexpensive media components, liquid fermentation is considered the most cost-effective method to produce fungal biocontrol agents.

Thus, a method of producing infectious fungal propagules in liquid culture is desirable. However, there are technical hurdles to be overcome. First, anamorphic hypocrealean entomopathogenic fungi such as *B. bassiana* and *I. fumosorosea* produce blastospores and not conidia in liquid culture. Although termed blastospores, these cells are actually vegetative, yeast-like cells and are not desiccation-tolerant and have a relatively limited shelf-life (Chong-Rodriquez et al., 2011; Lohse et al., 2014). Thus, the development of methodologies to produce desiccation-tolerant, shelf-stable blastospores in liquid culture, such that the blastospores could be utilized for pest-control is needed. Herein, we describe such methodologies.

Fungi are well known for their ability to metabolize a diverse array of compounds by expressing catabolic enzymes and permeases. After carbon and oxygen, nitrogen is the most abundant element in fungal cells and is one of the most expensive nutrients in the fermentation media. Identifying low-cost sources of nitrogen is critical in developing a suitable biopesticide production medium. Inexpensive nitrogen sources, such as cottonseed and soy flours, are generally unrefined containing mainly proteins and oligopeptides. These agricultural and food processing by-products are less expensive than more highly refined nitrogen sources such as acid or enzymatically hydrolyzed casein, soy hydrolyzates, or meat proteins, which contain high amounts of free amino acids. Previous studies have demonstrated the feasibility of producing blastospores of *I. fumosorosea* in short fermentation times (≤3 days) with good desiccation tolerance using more refined nitrogen sources such as acid hydrolyzed casein.

Because fungal entomopathogens possess a wide genetic variability and respond differently when growing in liquid media, suitable strain-specific parameters must be considered while evaluating and optimizing liquid culture production parameters. Work with *I. fumosorosea* has defined nutritional and environmental conditions that support the rapid production of high concentrations of desiccation tolerant blastospores with reasonable shelf life. However, the commercial use of blastospores of *B. bassiana* is nonexistent due to the requirement for long fermentation times and the poor desiccation tolerance and short shelf life of blastospore formulations. The production of dessication-tolerant blastospores, exhibiting shelf stability with concurrent bioefficacy as a biocontrol agent has not been previously achieved and is therefore desired.

SUMMARY OF THE INVENTION

In one embodiment of the invention, a method of producing a blastospore-containing composition is provided wherein the composition comprises desiccation-tolerant blastospores of a *Beauveria* species or an *Isaria* species produced by inoculating a liquid culture medium comprising a carbon source and a nitrogen source with fungal propagules of a *Beauveria* species or an *Isaria* species, incubating said propagules under culture conditions providing dissolved oxygen levels above zero and osmotic pressure greater than 0.5 MPa, incubating the propagules for a sufficient time to produce blastospores, collecting the blastospores; and drying the blastospores, thereby producing desiccation-tolerant blastospores. In some embodiments, the *Beauveria* species is *B. bassiana*. In other embodiments, the *Isaria* species is *I. fumosorosea*. In a particular embodiment, the carbon source is present in the liquid culture medium at an initial concentration of at least six percent. The carbon source can be glucose. In another particular embodiment, the nitrogen source is present in the liquid culture medium at an initial concentration of at least one and one-half percent. The nitrogen source can be cottonseed flour or hydrolyzed casein. In a specific embodiment, the carbon source is glucose and the nitrogen source is cottonseed flour.

Another embodiment provided herein is an insecticidal composition, comprising an agronomically acceptable carrier and desiccation-tolerant blastospores of a *Beauveria* species or an *Isaria* species, wherein the carrier and the blastospores are contained in air-tight packaging and wherein the blastospores are produced by inoculating a liquid culture medium comprising a carbon source and a nitrogen source with fungal propagules of a *Beauveria* species or an *Isaria* species, incubating the propagules under culture conditions providing dissolved oxygen levels above zero and osmotic pressure greater than 0.5 MPa, incubating the propagules for a sufficient time to produce blastospores, collecting the blastospores, and drying the blastospores, thereby producing desiccation-tolerant blastospores. In some embodiments, the *Beauveria* species is *B. bassiana*. In other embodiments, the *Isaria* species is *I. fumosorosea*. In some instances, an insecticidal composition also contains an oxygen scavenging compound, a moisture scavenging compound, or a combination of both. In some embodiments, greater than 60% of the blastospores are viable when rehydrated after storage for more than six months. In a particular embodiment, the insecticidal composition can be stored at temperatures of 28° C. or lower.

In still another embodiment of the present invention, a method for insect control is provided, the method comprising applying to the site of said insects an insecticidally effective amount of desiccation-tolerant blastospores of a *Beauveria* species or an *Isaria* species. In some instances, desiccation tolerant blastospores are produced by the method described above. In some embodiments, the *Beauveria* species is *B. bassiana*. In other embodiments, the *Isaria* species is *I. fumosorosea*. In a particular embodiment, during growth of the blastospores, the carbon source is glucose and the nitrogen source is cottonseed flour or hydrolyzed casein. The site of the insects can be an agricultural crop.

INCORPORATION BY REFERENCE

All publications, patents and patent applications mentioned in this specification are herein incorporated by reference to the same extent as if each individual publication, patent or patent application was specifically and individually indicated to be incorporated by reference.

BRIEF DESCRIPTION OF THE DRAWINGS

The patent or application file contains at least one drawing executed in color. Copies of this patent or patent application publication with color drawing(s) will be provided by the U.S. Patent and Trademark Office upon request and payment of the necessary fee.

The novel features of the invention are set forth with particularity in the claims. Features and advantages of the present invention are referred to in the following detailed description, and the accompanying drawings of which:

DETAILED DESCRIPTION OF THE INVENTION

Figure 1:
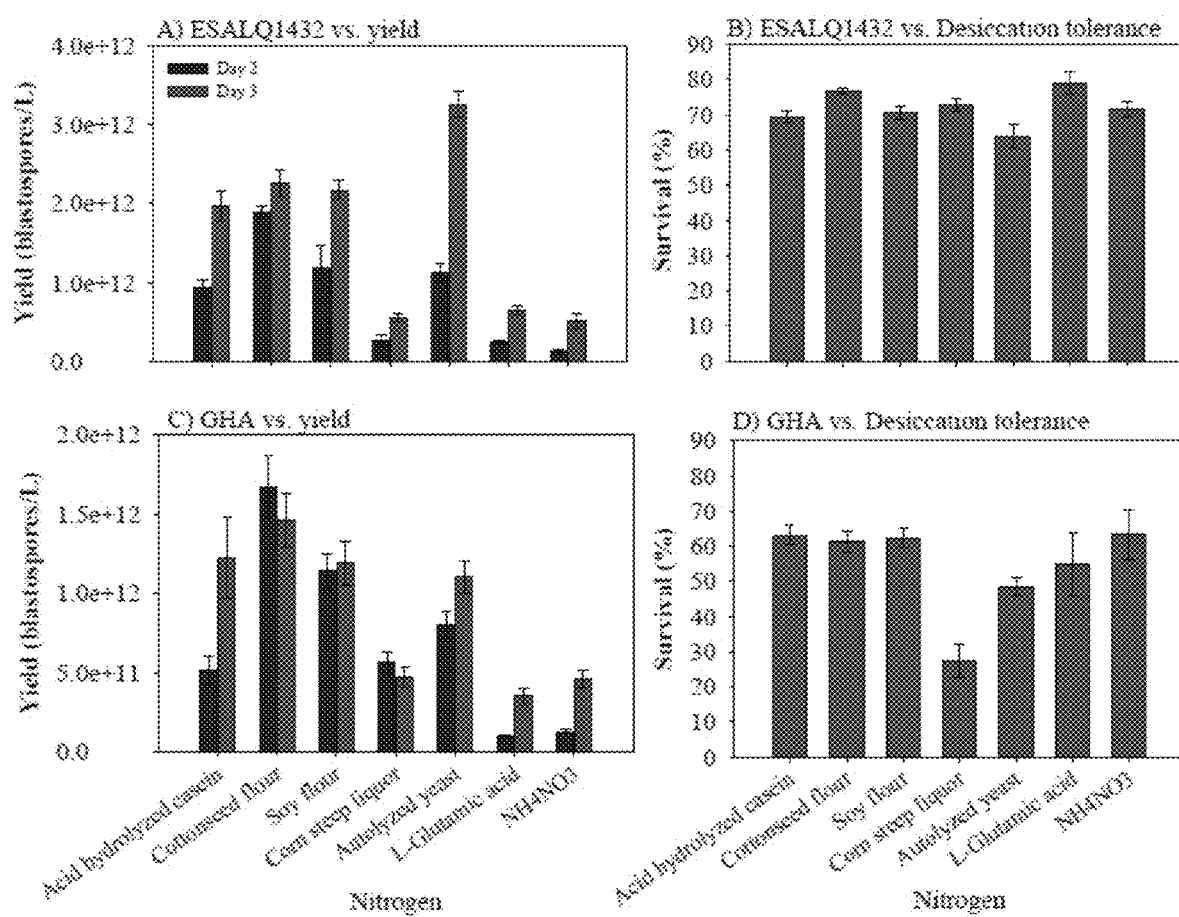
FIG. 1 provides a graphic representation of blastospore production and blastospore desiccation tolerance by *B. bassiana* isolates GHA and ESALQ1432 produced utilizing different nitrogen sources in liquid culture.

Preferred embodiments of the present invention are shown and described herein. It will be obvious to those skilled in the art that such embodiments are provided by way of example only. Numerous variations, changes, and substitutions will occur to those skilled in the art without departing from the invention. Various alternatives to the embodiments of the invention described herein may be employed in practicing the invention. It is intended that the included claims define the scope of the invention and that methods and structures within the scope of these claims and their equivalents are covered thereby.

Technical and scientific terms used herein have the meanings commonly understood by one of ordinary skill in the art to which the instant invention pertains, unless otherwise defined. The terminology used in the description of the invention herein is for describing particular embodiments only and is not intended to be limiting of the invention. As used in the description of the invention and the appended claims, the singular forms "a," "an," and "the" are intended to include the plural forms as well, unless the context clearly indicates otherwise.

Unless otherwise indicated, all numbers expressing quantities of ingredients, properties such as molecular weight, reaction conditions, and so forth as used in the specification and claims are to be understood as being modified in all instances by the term "about." Accordingly, unless otherwise indicated, the numerical properties set forth in the following specification and claims are approximations that may vary depending on the desired properties sought to be obtained in embodiments of the present invention. Notwithstanding that the numerical ranges and parameters setting forth the broad scope of the invention are approximations, the numerical values set forth in the specific examples are reported as precisely as possible. Any numerical values, however, inherently contain certain errors necessarily resulting from error found in their respective measurement. The term "about" is defined as plus or minus ten percent of a recited value. For example, about 1.0 g means 0.9 g to 1.1 g.

The terms isolated, purified, or biologically pure as used herein, refer to material that is substantially or essentially free from components that normally accompany the referenced material in its native state.

The term "shelf stable" and grammatical variations thereof, as herein described generally refers to air dried or spray dried (less than 5% moisture) blastospores demonstrating viability of one year or more when stored at 4° C., wherein viability is measured as at least about 60% germination after rehydrating and incubating the dried blastospores in an appropriate liquid media for 6-7 hours.

The term "desiccation tolerant" and grammatical variations thereof, as herein described generally refers to dried blastospores which show 50% or more germination when rehydrated and grown in appropriate medium, such as potato dextrose broth, within six to seven hours incubation.

Fungal entomopathogens are considered the frontline of biorational tools to manage populations of numerous insect pests including whiteflies with the potential to be integrated with application of synthetic chemical insecticides in order to mitigate development of insect resistance to insecticides. A large body of literature has focused on the use of aerial conidia of *B. bassiana* and *I. fumosorosea* deployed as contact bioinsecticides for the control of whiteflies. Several studies demonstrated that the yeast phase (blastospore) of *I. fumosorosea* was more effective than aerial conidia in controlling whiteflies, subterranean termites, planthoppers, aphids and beetles. In our recent whitefly control study using aerial conidia, we identified virulent Brazilian isolates of *B. bassiana* and *I. fumosorosea* that were efficacious in infecting and killing various life stages of the silverleaf whitefly *Bemisia tabaci* biotype B (Hemiptera: Aleyrodidae).

Herein is described a liquid culture fermentation method for producing desiccation tolerant, shelf stable blastospores under liquid culture conditions. In a favored embodiment, the culture conditions include high aeration rates, osmotic pressure of at least 0.5 Megapascal (MPa), at least 1.5% of a suitable nitrogen source, and at least 6% of a suitable carbon source. The liquid culture techniques can be used in the growth of entomopathogenic species of the genus *Beauveria* to promote the aforementioned qualities of shelf stability, desiccation tolerance and improved bioefficacy against insect pathogens. *Beauveria* species which can be utilized with the liquid culture fermentation method as described include *Beauveria alba, Beauveria amorpha, Beauveria arenaria, Beauveria asiatica, Beauveria australis, Beauveria bassiana, Beauveria brongniartii, Beauveria brumptii, Beauveria caledonica, Beauveria chiromensis, Beauveria coccorum, Beauveria cretacea, Beauveria cylindrospora, Beauveria delacroixii, Beauveria densa, Beauveria dependens, Beauveria doryphorae, Beauveria effusa, Beauveria epigaea, Beauveria felina, Beauveria geodes, Beauveria globulifera, Beauveria heimii, Beauveria kipukae, Beauveria taxa, Beauveria malawiensis, Beauveria melolonthae, Beauveria nubicola, Beauveria oryzae, Beauveria paradoxa, Beauveria paranensis, Beauveria parasitica, Beauveria petelotii, Beauveria pseudobassiana, Beauveria rileyi, Beauveria rubra, Beauveria shiotae, Beauveria sobolifera, Beauveria spicata, Beauveria stephanoderis, Beauveria sulfurescens, Beauveria sungii, Beauveria tenella, Beauveria tundrensis, Beauveria velata, Beauveria varroae, Beauveria vermiconia, Beauveria vexans, Beauveria viannai, Beauveria virella*. Other filamentous entomopathogenic fungi that are dimorphic including *Metarhizium* spp., *Hirsutella* spp., *Lecanicillium* spp., *Isaria* spp., and *Nomuraea* spp. will likely produce blastospores effectively and profusely using the present growing conditions comprised by the combination of high aeration, osmotic pressure, and appropriate nitrogen source and concentration.

The blastospores of the entomopathogenic fungi of this invention can be utilized for infecting and killing a wide variety of economically important arthropods, including ground-, soil- and canopy-dwelling insects. Without being limited thereto, arthropods which may be controlled by the compositions of this invention include root weevils, rootworms, wireworms, fruit flies, soil grubs, root maggots, termites, ticks, fleas, grasshoppers, ants, and a variety of other insects of agricultural, horticultural, medical and veterinary importance. Some non-limiting examples of target insects include, corn rootworm (*Diabrotica* spp), black vine weevil (*Otiorhynchus sulcatus*), citrus root weevil (*Diaprepes abbreviatus*), sweet potato weevil (*Cylas formicarius*), sugarbeet root maggot (*Tetanops myopaeformis*), cabbage maggot (*Delia radicum*), onion maggot (*Delia antigua*), turnip maggot (*Delia floralis*), seedcorn maggot (*Delia platura*), carrot rust fly (*Psila rosae*), Japanese beetle (*Popillia japonica*), European chafer (*Rhizotrogus majalis*), subterranean termite (*Reticulitermes* and *Coptotermes* spp.), emerald ash borer (*Agrilus planipennis*), gypsy moth (*Lymantria dispar*), and the pecan weevil (*Curculio caryae*), tobacco caterpillar (*Spodoptera litura*), tobacco budworm, cotton bollworm (*Helicoverpa armigera*), fall armyworm (*Spodoptera frugiperda*), corn ear worm (*Helicoverpa zea*), European corn borer (*Ostrinia nubilalis*), Asian corn borer (*Ostrinia furnacalis* Guenee) sorghum stem borers (*Chilo partellus, Coniesta ignefusalis, Busseola fusca, Chilo* spp.), yellow stem borer of rice (*Scirpophaga incertulas*), rice leaffolder (*Cnaphalocrocis medinalisi*), brown plant hopper of rice (*Nilaprvata lugens*), rice thrips (*Stenchaetothrips biformis*), leaf hopper (*Hishimonus phycitis*), grasshoppers (*Melanoplus* spp.), cactus weevil (*Metamasius spinolaei*), silverleaf whitefly (*Bemisia argentifolii*), beet armyworm (*Spodoptera exigua*), cucumber beetle (*Diabrotica undecimpunctata*), alfalfa looper (*Autographa californica*), cotton aphid (*Aphis gossypii*), termites (*Odontotermes obesus, Odontotermes* spp., *Trinervitermes biformis*), jassid (*Emboasca kerri*), thrips (*Frankliniella schultzei, Scirtothrips dorsalis, Podothrips bicolor*), diamondback moth (*Plutella xylostella*), green peach aphid (*Aphis gossypii*), potato aphid (*Macrosiphum euphorbiae*), thrips (*Anephothrips dorsalis, Thrips palmi*), mealy bug (*Maconellicoccus hirsutus*), grass hopper (*Melanoplus* spp.), whitefly (*Bemisia tabaci*), brinjal shoot borer (*Leucinodes orbonalis*), stem borers, beet armyworm, (*Spodoptera exigua, Spodoptera* spp.), cabbage looper (*Trichoplusia ni, Trichoplusia* spp.), spiny bollworm (*Earias insulana*), spotted bollworm (*Earias vitella*), leaf roller (*Sylepta derogata*), mites (*Leyranychus telari*), okra jassid (*Amrasca biguttula*), mosquito (*Anopheles gambiae, Culex quinquefasciatus*), house fly (*Musca domestica*), cockroaches (*Periplanata americana*) and ticks (*Ixodes dammini*), *Triatoma infestans, Rhodnius prolixus*, ticks—soft tick (*Argas persicargas persicus*), bovine tick (*Rhipicephalus microplus*), *Babesia microti*, blacklegged tick or deer tick (*Ixodes scapularis*), sheep scab mite (*Psoroptes ovis*), tropical fowl mite (*Ornithonyssus bursa*), fleas—Siphonaptera, Cat flea (*Ctenocephalides felis*) and cattle louse (*Haemaptopinus eurysternus*).

Culture Conditions

Fungi useful in practicing the present invention, specifically *B. bassiana* and *I. fumosorosea*, exhibit polymorphic forms ranging from conidia to pseudohyphae, hyphae, and blastospores (yeast-like vegetative cells), depending on isolate differences, age, medium and culture conditions. Like most fungi, culture conditions under which they are grown, affect multiple aspects of the biology of the organism, including morphological form and bioproduct spectrum.

Thus, one of skill in the art will recognize that multiple culture conditions can be modified in practicing the invention disclosed herein. Non-limiting examples of culture conditions that can be modified during the application and practice of the inventions disclosed herein, include: 1) temperature; 2) primary carbon source; 3) oxygen concentration; 4) primary nitrogen source; 5) pH; 6) mineral and other ion concentration; 7) age/growth phase of culture; 8) organization of an industrial fermenter; and 9) predominant morphological form. One of skill in the art will recognize that other culture parameters affecting desired bioproduct production and bioproduct yield can be modified.

In one aspect of the invention, cultures of fungal strains described herein can be grown at any temperature that facilitates the production of one or more bioproducts. For example, a culture can be grown at a temperature of 15°-30° C., or any whole or partial degree within that range, including, but not limited to 15.0° C., 15.5° C., 16.0° C., 16.5° C., 17.0° C., 17.5° C., 18.0° C., 18.5° C., 19.0° C., 19.5° C., 20.0° C., 20.5° C., 21.0° C., 21.5° C., 22.0° C., 22.5° C., 23.0° C., 23.5° C., 24.0° C., 24.5° C., 25.0° C., 25.5° C., 26.0° C., 26.5° C., 27.0° C., 27.5° C., 28.0° C., 28.5° C., 29.0° C., 29.5° C., and 30.0° C.

In some embodiments, the fungal strains described herein can be grown under conditions where the pH of the culture facilitates the production of one or more morphological forms of interest. For example, a culture can be grown in media where the pH is between 3.0 and 8.5, 4.5 and 6.5, or any value within that range, including, but not limited to pH 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5. One of skill in the art will recognize that a stable pH does not need to be maintained throughout the entirety of the growth of the strain producing the bioproduct(s) of interest. Thus, in some embodiments, the pH of a microbial culture of the present invention will vary. In other embodiments, pH buffers can be added to maintain a relatively stable pH where the pH of the culture medium over the life of the culture does not vary from a chosen starting point by more than ±0.5.

In some embodiments, microbial strains of the present invention can be grown in the presence of particular carbon sources. For example, a culture can be grown in the presence of simple carbon sources such as (D- or L-) arabitol, sucrose, fructose, glucose, mannose, galactose, arabinose, arabinose, xylose, mannitol, glucitol, galactitol, xylitol, ribitol, threitol, glycerol, gluconic acid, glucosamine, or meso-erythritol.

Alternately, a culture can be grown in the presence of complex carbon sources such as cellulose, starch, beet molasses, carob pod, cornmeal hydrolysates, corn syrup, fuel ethanol fermentation stillage, grape skin pulp, vegetable oils, peat hydrolysate, hydrolyzed potato starch, and spent sulfite liquor. Carbon sources that are also sources for other nutritional requirements, such as nitrogen, can be utilized. For example, media for use in the present invention can include amino acids such as aspartate, threonine, lysine, methionine, isoleucine, asparagine, glutamic acid, glutamine, proline, alanine, valine, leucine, tryptophan, tyrosine, phenylalanine and their metabolic intermediates. These lists are non-limiting and it is well within the capabilities of one of skill in the art to utilize other carbon sources in practicing the present invention. Any carbon source can be used alone or in combination with other carbon sources.

Other nutritional parameters can also be varied, including nitrogen sources. Non-limiting examples of nitrogen sources include organic nitrogen sources (e.g., cottonseed flour, acid hydrolyzed casein, autolyzed yeast, glutamic acid, peptone, soybean pomace, yeast extract, food gravy, malt extract, corn steep liquor and soybean flour) and inorganic nitrogen sources (e.g, urea, ammonium sulfate, ammonium chloride, ammonium phosphate, ammonium carbonate and ammonium nitrate) can be included in growth media utilized in the practice of the present invention. In some embodiments, a nitrogen source is present in an amount of 1%, 1.5%, 2%, 2.5%, 3%, 3.5%, 4%, 4.5%, 5%, 5.5%, 6%, 6.5%, 7%, 7.5%, 8%, 8.5%, 9%, 9.5%, 10%, 10.5%, 11%, 11.5%, 12%, 12.5%, 13%, 13.5%, 14%, 14.5%, 15% or more. Preferably, the concentration is between 1.5% and 9%.

Phosphate sources such as potassium dihydrogen phosphate, dipotassium hydrogen phosphate and their corresponding sodium-containing salts can be included in growth media as necessary. Metal and mineral salts such as salts of zinc, iron, magnesium, manganese, calcium and copper can be included as needed. Other nutritional supplements, such as vitamins (e.g, biotin, thiamine) can also be included. One of skill in the art will recognize that varying culture nutritional makeup can be utilized to maximize production of a bioproduct of interest and decrease production of undesired by-products. Any of these nutrients can be used alone or in combination with any other nutrient.

In some embodiments, osmolytes are used to control the osmotic pressure of the liquid culture. Osmolytes such as sugars (glucose, galactose, fructose, trehalose etc.), polyols (mannitol, glycerol, erythritol etc.), proteins, amino acids, salts, polymers (polyvinylpyrrolidone, polyethylene glycol etc.), and any compound that can be used to change the osmotic pressure in liquid culture media for submerged fermentation can be utilized. Generally, according to the present invention, improvements in blastospore form and production are achieved by increasing osmotic pressure >0.5 MPa.

In a particular embodiment of the present invention liquid culture techniques for producing desiccation tolerant spores utilizes concentrations of at least a 1.5%-9% nitrogen source and at about 4%-25% carbon source, with at least 0.5 MPa osmotic pressure.

Nutrients can be added to the culture in any feeding regimen, including, but not limited to high cell-density culture, batch culture, fed-batch culture, constantly-fed-batch culture, exponentially-fed batch culture, continuous culture, or a mixture of these approaches for different nutrients.

In some instances, the length of time a culture is grown can be modified to enhance or begin production of a bioproduct of interest. For example, a culture can be grown for 10-300 hours, or more, or any time point within that range, for example 10, 20, 30, 40, 50, 60, 70, 80, 90, 100, 110, 120, 130, 140, 150, 160, 170, 180, 190, 200, 210, 220, 230, 240, 250, 260, 270, 280, 290, 300 hours, or more before harvesting of a bioproduct commences.

In liquid cultures under agitation, cultures of the present invention can be grown so as to increase dissolved oxygen. Factors that affect dissolved oxygen levels include culture volume, container volume, rotation speed and, in a fermentor, aeration rate, agitator speed, impellor design, fermentation tank design, tank head pressure, and aeration gas mixture. In some embodiments, a culture can be shaken on a rotary shaker at any viable speed from 50-400 rpm. Aeration rates for fermentors can be at any viable rated from zero to 700 standard liters per minute (slpm), including, but not limited to 50, 100, 150, 200, 250, 300, 350, 400, 450, 500, 550, 600, 650, 700 or more slpm. Agitator speed can be from 50-1000 rpm depending on the fermentor size. Fermentor head pressure can vary from 0-30 psi to increase dissolved oxygen levels. Aeration gas mixtures can vary in oxygen content from normal air, which is 21% oxygen, to pure oxygen. Dissolved oxygen levels in preferred embodiments will be maintained above zero.

Additionally, optimization of fungal cell production can depend on growing a culture to a particular point in the life cycle. For example, a culture can be grown to early lag phase, middle lag phase, late lag phase, early exponential phase, mid-exponential phase, late exponential phase, early stationary phase, mid-stationary phase, or death phase. In some instances, cultures can be maintained in a growth phase (e.g., by fed-batch culture) in order to maintain a particular growth phase for the culture.

In other instances, culture conditions can be altered so that one morphological form of the fungal strains predominates over other morphological forms. For example, culture conditions can be controlled so that yeast-like forms (blastospores) predominate, conidia predominate, or hyphae/pseudohyphae predominate.

In some preferred embodiments, blastospores produced utilizing the present invention can be dried prior to usage as a biocontrol agent. For air-drying blastospores, culture broth containing blastospores (2-5 day fermentation) are harvested from the culture broth by filtration, centrifugation, or any other means known in the art to remove spent medium. Blastospores can be mixed with a suitable filter aid such as, but not limited to, clay, diatomaceous earth, talc, silicon dioxide, or calcium silicate. This mixture can be vacuum-filtered to remove spent media and forming a filter cake. Filter cakes can be broken apart using any suitable granulation equipment. The granulated blastospore filter cake is then dried using air drying, vacuum drying, or fluidized bed drying to a final moisture content of less than 5% or water activities ($a_w$) below 0.3. Alternately, spray drying or fluidized bed drying of blastospores is performed by spray drying blastospore-containing culture broth or separated blastospore suspensions with or without carriers or stabilizers. Carriers or stabilizers can include compounds that improve the flowability, suspendability, desiccation tolerance, and/or storage stability of the blastospore formulation and may include but are not limited to proteins, carbohydrates, skim milk, maltodextrin, disaccharides, simple sugars, molasses, PVP, clays, diatomaceous earth, talc, silicon dioxide, or calcium silicate. Spray drying is conducted at inlet/outlet temperatures that minimize blastospore exposure to high temperatures and that result in a flowable blastospore formulation dried to less than 6% moisture. Spray drying protocols such as the use of 90° C. inlet/50° C. outlet temperatures are preferred. Other spray drying inlet/outlet temperature protocols are suitable as long as the dried blastospore formulation is only briefly exposed to high temperatures. Fluidized bed drying could employ the previously described carriers and be operated at temperatures conducive to spore survival.

Biocontrol Compositions

In some embodiments, blastospores produced by methods of the present invention are combined with one or more other components to produce a biocontrol composition, typically for use as an insecticide. In some instances, the biocontrol composition comprises at least one agriculturally acceptable carrier. Some non-limiting examples of such carriers include filler stimulants, anti-caking agents, wetting agents, emulsifiers, nutritional amendments and antioxidants. Such carriers can be used alone or in any combination. One of skill in the art is capable of choosing appropriate carriers for particular applications. Filler stimulants can be a carbohydrate source, such as a disaccharide including, for example, trehalose and sucrose, or monosaccharides such as fructose or glucose. Potential anti-caking agents can include talc, silicon dioxide, calcium silicate, or kaolin clay. Wetting agents include, but are not limited to surfactants or skim milk powder. Emulsifiers can include soy-based emulsifiers such as lecithin or vegetable-based emulsifiers such as monodiglyceride. Antioxidants can include, but are not limited to, sodium glutamate, ascorbic acid and citric acid.

In various embodiments, the biocontrol composition is a stable composition capable of supporting reproductive viability of the fungal cell component, or capable of retaining insecticidal efficacy for a period of between 2 weeks and 2 years. In some instances this period is about 2 weeks, about 3 weeks, about 4 weeks, about one month, about two months, about three months, about four months, about five months, about six months, about seven months, about eight months, about nine months, about ten months, about eleven months, about twelve months, about thirteen months, about fourteen months, about fifteen months, about sixteen months, about seventeen months, about eighteen months, about nineteen months, about twenty months, about twenty-one months, about twenty-two months, about twenty-three months, about twenty-four months, or more. Such storage periods can be achieved at any storage temperature between 0-35° C.

To facilitate long-term storage, in some embodiments, components such as oxygen scavengers, and moisture scavengers (desiccants) can be utilized in conjunction with the packaging of the composition. Typically, the packaging is an air- and water-tight design. The particular material of the packaging is not important to the invention and any commercially available material can be utilized for packaging, such as sealable aluminum films or mylar films. A desiccant is a hygroscopic substance usually in a porous pouch or sachet which is placed inside a sealed package. Favored desiccants are chemically stable or chemically inert, and include silica gel, activated charcoal, calcium sulfate (Drierite), calcium chloride, molecular sieves (typically, zeolites), incozol 2, Loxanol®, Byk®-2616, Trixene AS, Tyzor® IBAY, AMP 95, AMPD, Sylosiv®A3, Silquest®A-171, NEWOTEC®547, USI®-SL25, Modarez®, Zeolum®, TAFTIC™, and the like. Oxygen scavengers can include any effective substance which absorbs oxygen, typically via an oxidation reaction. Non-limiting examples of oxygen scavengers that can be utilized in the present invention include enzyme-mediated oxidation (Bioka®S-100, Bioka®S-75), iron-based oxidation (Ageless®FX-100, FreshPax®), ascorbate, sodium hydrogen carbonate, and the like.

Biocontrol compositions of the present invention can be utilized in combination with other components which can collectively be termed agrochemicals. Examples of the categories of agrochemicals that can be combined with the fungal propagules of the present invention include, but are not limited to germicides, herbicides, insecticides and miticides, plant growth regulators, biostimulants, fungicides, and the like. Such additional components can be utilized alone or in any combination.

In some instances, a biocontrol composition of the present invention also comprises blastospores of an entomopathogenic fungus and one or more germicides can include: captan, thiuram, ziram, zineb, maneb, mancozeb, propineb, polycarbamate, chlorothalonil, quintozene, captafol, iprodione, procymidone, fluoroimide, mepronil, flutolanil, pencycuron, oxycarboxin, fosetyl-aluminum, propamocarb, triadimefon, triadimenol, propiconazole, diclobutrazol, bitertanol, hexaconazole, myclobutanil, flusilazole, etaconazole, fluotrimazole, flutriafen, penconazole, diniconazole, cyproconazole, fenarimol, triflumizole, prochloraz, imazalil, pefurazoate, tridemorph, fenpropimorph, trifolin, buthiobate, pyrifenox, anilazine, polyoxin, metalaxyl, oxadixyl, furalaxyl, isoprothiolane, probenazole, pyrrolnitrin, blasticidin S, kasugamycin, validamycin, dihydrostreptomycin sulfate, benomyl, carbendazim, thiophanate-methyl, hymexazol, basic copper chloride, basic copper sulfate, fentin acetate, triphenyltin hydroxide, diethofencarb, quinomethionate, binapacryl, lecithin, sodium bicarbonate, dithianon, dinocap, fenaminosulf, diclomezine, guazatine, dodine, IBP, edifenphos, mepanipyrim, ferimzone, trichlamide, methasulfocarb, fluazinam, ethoquinolac, dimethomorph, phylloquinone, tecloftalam, phthalide, phenazine oxide, thiabendazole, tricyclazole, vinclozolin, cymoxanil, cyclobutanyl, guazatine, propamocarb hydrochloride, oxolinic acid, cyflufenamid, iminoctadine, kresoxim-methyl, triazine, fenhexamid, cyazofamid, cyprodinil, prothioconazole, fenbuconazole, trifloxystrobin, azoxystrobin, hexaconazole, imibenconazole, tebuconazole, difenoconazole, carpropamid, and the like. One of skill in the art will recognize that this is not an exhaustive list and any agronomically or horticulturally acceptable germicide can be utilized.

In some instances, a biocontrol composition of the present invention comprises blastospores of an entomopathogenic fungus and one or more herbicides including, but not limited to: 2,4-D, MCPA, clomeprop, dicamba, chlorotoluron, diuron, linuron, isouron, fenuron, neburon, simazine, atrazine, simetryn, prometryn, hexazinone, propazine, desmetryne, terbumeton, propanil, bromoxynil, ioxynil, pyridate, chloridazon, bentazon, chlomethoxyfen, bifenox, sodium acifluorfen, flumioxazin, thiadiazine, oxadiazon, sulfentrazone, pentoxazone, pyraclonil, pyrazolynate, pyrazoxyfen, benzofenap, mesotrione, isoxaflutole, isoxachlortole, amitrole, aclonifen, diflufenican, benzobicyclon, diclofop-methyl, fluazifop-butyl, alloxydim sodium, clethodim, sethoxydim, tralkoxydim, tepraloxydim, bensulfuron-methyl, pyrazosulfuron-ethyl, rimsulfuron, imazosulfuron, prosulfuron, fulmetsulam, diclosulam, metosulfam, imazapyr, imazaquin, pyrithiobac-sodium, bispyribac-sodium, pyriminobac-methyl, flucarbazone, propoxycarbazone, glyphosate, a glyphosate ammonium salt, gluphosinate, trifluralin, pendimethalin, benfluralin, prodiamine, propham, dithiopyr, alachlor, metolachlor, pethoxamid, acetochlor, propachlor, dimethenamid, diphenamid, napropamide, mefenacet, fentrazamide, molinate, dimepiperate, cycloate, esprocarb, thiobencarb, thiocarbazil, bensulide, dalapon, asulam, DNOC, dinoseb, flupoxam, triaziflam, quinclorac, cinmethylin, dazomet, dymron, etobenzanide, oxaziclomefone, pyributicarb, and the like. One of skill in the art will recognize that this is not an exhaustive list and any agronomically or horticulturally acceptable herbicide can be utilized.

In some instances, a biocontrol composition of the present invention comprises blastospores of an entomopathogenic fungus and one or more plant growth regulators include gibberellins (for example, gibberellin A3, gibberellin A4, and gibberellin A7), IAA, NAA, and the like. One of skill in the art will recognize that this is not an exhaustive list and any agronomically or horticulturally acceptable plant growth regulator can be utilized.

In some instances, a biocontrol composition of the present invention comprises blastospores of an entomopathogenic fungus and one or more chemical insecticides. One of skill in the art is able to choose one or more chemical insecticides as appropriate for control of one or more insect pest species. Such chemical insecticides can include the following: Acetylcholinesterase inhibitors (carbamates, organophosphates), GABA-gated chloride channel blockers (cyclodiene organochlorines, phenylpyrazoles), sodium channel modulators (pyrethroids, pyrethrins), nicotinic acetylcholine receptor competitive modulators (neonicotinoids, nicotine, sulfoxaflor, buetnolides), nicotinic acetylcholine receptor allosteric modulators (spinosyns), glutamate-gated chloride channel allosteric modulators, juvenile hormone mimics (hormone analogs, fenoxycarb, pyriproxyfen), non-specific (multi-site) inhibitors (alkyl halides, chloropicrin, sulfuryl fluoride, borates, tartar emetic, methyl isothiocyanate generators), modulators of chordotonal organs (pymetrozine, flonicamid), mite growth inhibitors (clofentezine, diflovidazin, hexythiazox, etoxazole), mitochondrial ATP synthase inhibitors (diafenthiuron, organotin miticides, propargite, tetradifon), chloride channel activators (avermectin, milbemycin), proton gradient disruptors/oxidative phosphorylation uncouplers (chlorfenapyr, DNOC, sulfluramid), nicotinic acetylcholine receptor channel blockers (nereistoxin analogues), chitin biosynthesis inhibitors (benzoylureas, buprofezin), molting disruptors (cryomazine), ecdysone receptor agonists (diacylhydrazines), octopamine receptor agonists (amitraz), electron transport inhibitors (hydramethylnon, acequinocyl, fluacrypyrim, METI acaricides, rotenone, phosphine, cyanides, β-ketonitrile derivatives, carboxanilides), voltage-dependent sodium channel blockers (indoxacarb, metaflumizone), acetyl CoA carboxylase inhibitors (tetronic and tetramic acid derivatives), ryanodine receptor modulators (diamides), and compounds of uncertain modes of action (azadirachtin, benzoximate, bifenazate, bromopropylate, chinomethionate, cryolite, dicofol, pyridalyl, pyrifluquinazon, sulfur, lime sulfur). One of skill in the art will recognize that this is a non-limiting list of potential insecticides, and that any agronomically or horticulturally acceptable pesticide can be utilized.

In still other embodiments, a biocontrol composition of the present invention comprises blastospores of an entomopathogenic fungus and one or more fungicides, for example: mancozeb, tricyclazole, carbendazim, hexaconazole, metalaxyl, benomyl, difenoconazole, propiconazole, kitazin, tebuconazole, copper oxychloride, copper hydroxide, tridemorph, propineb, safin, sporrin, blastin, bio-vitrioll and the like. Typically, a fungicide used will have little or no activity against the fungal blastospores of the composition. One of skill in the art will recognize that this is not an exhaustive list and any agronomically or horticulturally acceptable plant growth regulator can be utilized.

Biocontrol composition formulations for use as an insect control agent may be prepared from blastospores that have been harvested from the culture medium such as described hereinabove. As a practical matter, it is envisioned that such formulations may be prepared directly from the culture, thereby obviating the need for any purification steps. While liquid cultures can be used directly, in the preferred embodiment the water is removed from the cultures to partial or substantial dryness as described above, and the dried culture broken or ground into small particles suitable for application through conventional granule applicators, using techniques conventional in the art. Drying can be performed via air drying (such as mixing collected blastospores with a desiccating agent such as diatomaceous earth) or spray drying.

To facilitate application and subsequent fungal outgrowth, the harvested blastospores can alternatively be formulated in a suitable, agronomically acceptable, nutritional or inert carrier or vehicle for application as wettable powders, dusts, granules, baits, solutions, emulsifiable concentrates, emulsions, suspension concentrates and sprays (aerosols). For example, for liquid applications, the biocontrol compositions can be formulated as a suspension or emulsion. In such embodiments, preferred carriers include but are not limited to water, buffers, or vegetable or plant oils. In an alternative, preferred embodiment particularly suited for solid granular applications, the biocontrol compositions can be formulated with solid inert carriers or diluents such as diatomaceous earth, talc, clay, vermiculite, $CaCO_3$, corn cob grits, alginate gels, starch matrices or synthetic polymers, or they may be incorporated into conventional controlled release microparticles or microcapsules. The skilled practitioner will recognize that the fungi may also be formulated in combination with conventional additives such as sticking agents or adherents, emulsifying agents, surfactants, foams, humectants, or wetting agents, antioxidants, UV protectants, nutritive additives, fertilizers, insecticides, or even with fungicides which exhibit low toxicity to the subject fungi. For application onto the bark or canopy of trees and plants, the biocontrol compositions can also be formulated with a hygroscopic or hydrophilic adjuvant.

The absolute amount of the blastospores and their concentration in the final composition can be selected to provide an effective reduction in the population of the target insect as compared to an untreated control. The actual amount is not critical and is a function of practical considerations such as the properties of the vehicle or carrier, the density of the target insect population, and the method and site of application, and may be readily determined by routine testing. As the blastospores of this invention serve to produce and deliver a high concentration of the infective vegetative fungal cells to control the target insects by infection and death, for purposes of formulation and application, an "effective amount" is defined to mean any quantity of blastospores sufficient to subsequently produce enough cells in the target habitat to infect and kill the target insect relative to an untreated control. By way of example and without being limited thereto, it is envisioned that suitable formulations will typically contain about $1 \times 10^6$ or higher blastospores per gram of biomass recovered from the liquid culture (based on the dried weight of the biomass), preferably at least $1.5 \times 10^7$ blastospores per gram of biomass. For application to typical row crops, without being limited thereto, it is envisioned that suitable application rates are at least $1 \times 10^7$ blastospores per hectare. In other embodiments, the application rate can be at least $1 \times 10^6$, $5 \times 10^6$, $1 \times 10^7$, $5 \times 10^7$, $1 \times 10^8$, $5 \times 10^8$, $1 \times 10^9$, $5 \times 10^9$, $1 \times 10^{10}$, $5 \times 10^{10}$, $1 \times 10^{11}$, $5 \times 10^{11}$, $1 \times 10^{12}$, $5 \times 10^{12}$, $1 \times 10^{13}$, $5 \times 10^{13}$, $1 \times 10^{14}$, $5 \times 10^{14}$, $1 \times 10^{15}$, $5 \times 10^{15}$, $1 \times 10^{16}$, $5 \times 10^{16}$, or more blastospores per hectare.

In use, the biocontrol compositions of this invention can be applied to the locus or vicinity of the target insects or on the surface of the plants to be protected, e.g., onto tree bark, or as a seed coating, using conventional techniques. In a preferred embodiment, the blastospores are applied to the soil, or to soil-less potting mixes such as are used in greenhouses, in a granular form and to above-ground plant surfaces in a sprayable suspension. Depending upon the target insect pest, the blastospores may be applied in agricultural fields, orchards, greenhouses, gardens or lawns, or on or in the vicinity of ornamental plants, trees, or commercial or residential structures. The biocontrol compositions can be applied to the soil, to soil-less potting mixes, to plant surfaces, or a combination thereof.

Having described the invention in general, below are examples illustrating the generation and efficacy of the invention. Neither the examples, nor the general description above should be construed as limiting the scope of the invention.

EXAMPLES

Fungi and Inoculum Preparation

Five isolates of *B. bassiana* and five isolates of *I. fumosorosea* were tested in this study. The majority of the fungal isolates originated from Brazil with details given in Table 1. The isolates ARSEF 3581 of *I. fumosorosea* and GHA (ARSEF 6444) of *B. bassiana*, currently designated the active ingredient of the commercial bioinsecticide known as Mycotrol® (Laverlam, Butte, Mont., USA), served as U.S. standards for the liquid culture studies. Brazilian fungal isolates were previously identified using a molecular technique based on domain gene sequencing. Stock cultures of these fungi were grown on potato dextrose agar ([PDA] Difco®, Detroit, Mich., USA) in Petri dishes for 2-3 weeks at 22±2° C. with a 12:12 h (L:D) photoperiod until sporulation, cut into 1 $mm^2$ agar plugs and stored in 10% glycerol in sterile cryovials at −80° C. To produce conidial inoculum, frozen stock cultures were used to inoculate PDA plates that were incubated for 2-3 weeks until cultures sporulated on the plates.

TABLE 1

*B. bassiana* and *I. fumosorosea* isolates

| Fungus | Isolate Code | Host/Source |
| --- | --- | --- |
| B. bassiana | ESALQ-PL63 | Atta sp |
|  | ESALQ447 | Solenopsis invicta |
|  | ESALQ1432 | Diaphorina citri |
|  | CG1229 | Rupela albinella |
|  | GHA (ARSEF6444) | Diabrotica undecimpunctata |
| I. fumosorosea | ESALQ1296 | Bemisia tabaci |
|  | ESAL11364 | Myzus persicae |
|  | ESALQ1409 | B. tabaci |
|  | CG1228 | R. albinella |
|  | ARSEF3581 | B. tabaci |

Media and Culture Conditions

Liquid media used for pre-cultures and blastospore production contained the following basal salts per liter: $KH_2PO_4$, 2.0 g; $CaCl_2 \cdot 2H_2O$, 0.4 g; $MgSO_4 \cdot 7H_2O$, 0.3 g; $CoCl_2 \cdot 6H_2O$, 37 mg; $FeSO_4 \cdot 7H_2O$, 50 mg; $MnSO_4 \cdot H_2O$, 16 mg; $ZnSO_4 \cdot 7H_2O$, 14 mg; thiamin, riboflavin, pantothenate, niacin, pyridoxamine, thioctic acid, 500 mg each; folic acid, biotin, vitamin B12, 50 mg each. All chemicals used were obtained from Sigma® (St. Louis, Mo., USA) unless otherwise stated. The pre-culture basal salts medium was supplemented with glucose (Fisher Scientific®) at 80 g/L (40% carbon) and acid hydrolyzed casein (derived from bovine milk, Hy-case™ MSF, Kerry Bioscience, New York, N.Y., USA) at 25 g/L (8.5% N and 53% C), which produced a medium with a carbon-to-nitrogen ratio (C:N) of 23:1. The pre-culture medium had an initial pH of 5.8 and pH was not adjusted during culture growth. Glucose stock solutions (20% w/v) were autoclaved separately and added prior to inoculation. Sterilization of liquid cultures and glucose stock solutions were performed at 123° C. for 20 min. All media were prepared with distilled deionized water ($ddH_2O$). Conidial inocula for pre-cultures were harvested by scraping plates with 10 mL of sterile aqueous solution of 0.04% polyoxyethylene sorbitan mono-oleate (Tween® 80, Sigma®). Pre-cultures were inoculated with conidial suspensions to deliver a final concentration of $5 \times 10^5$ conidia per mL for *I. fumosorosea* and $1 \times 10^6$ conidia per mL for *B. bassiana* in the liquid culture medium. One hundred mL pre-cultures of all fungi were grown in 250-mL baffled, Erlenmeyer flasks (Bellco Glass, Vineland, N.J., USA) for 3 days at 28° C. and 350 rpm using a rotary incubator shaker (INNOVA 4000, New Brunswick Scientific, Edison, N.J.). Conidial and blastospore concentrations were measured microscopically using a haemocytometer (400× magnification) with a light microscope with DIC optics (BH2, Olympus America, Center Valley, Pa., USA).

Experimental Design for Liquid Fermentation Studies

To test for optimal nutritional components for further experimentation, several nitrogen sources were tested for their ability to induce blastospore production and desiccation tolerance. Nitrogen sources tested were 3% acid hydrolyzed casein, cottonseed flour, soyflour, autolyzed yeast, corn steep liquor, L-glutamic acid and 1% ammonium nitrate [$NH_4NO_3$]. All culture media contained 12% glucose. Fifty mL cultures were grown in 250-mL baffled Erlenmeyer flasks at 28° C. and 350 rpm for 3 days. Blastospores were separated from the culture broth with diatomaceous earth (7.5% w/v) and then air-dried to <4% moisture. Blastospore desiccation tolerance was assessed by measuring germination by air-dried blastospores rehydrated in potato dextrose broth and incubated for 7 hours at 28° C. and 300 rpm.

A factorial experimental design was used to investigate the impact of nitrogen source on different *B. bassiana* and *I. fumosorosea* isolates grown in submerged liquid cultures. *Isaria* and *Beauveria* cultures were grown in 100 mL volume in 250-mL Erlenmeyer flasks and incubated at 28° C. and 350 rpm in a rotary shaker incubator. The blastospore production medium contained the previously described basal salt medium supplemented with glucose (100 g/L) and either acid hydrolyzed casein or cottonseed flour (9.4% N and 40% C; Pharmamedia®, Traders Protein, Memphis, Tenn., USA) at a concentration of 25 g/L. The medium had an initial pH of 5.5 and a C:N ratio of 21:1. Blastospore inocula were obtained from 3-day-old pre-cultures (exponential phase) providing a final inoculum concentration of $5 \times 10^6$ blastospores/mL. Flasks were hand-shaken frequently during the fermentation process to minimize mycelial growth and sporulation on the flask walls. In all experiments, pH was uncontrolled during culture growth.

During culture broth sampling and dilution, blastospore suspensions were constantly vortexed to ensure homogeneity. Dry weight was used as a measure of biomass accumulation. Duplicate 1-mL culture broth samples were collected from flasks, the biomass separated from the spent medium by vacuum filtration (model 1225, Millipore®) onto pre-weighed 2.4-cm glass fiber filter disks (G6, Fisher Scientific®, Pittsburgh, Pa., USA), and then dried at 80° C. for 24 h until constant weight prior to measurement. At the end of the fermentation process, the remaining glucose (g/L) was measured using a glucose meter (GlueCell®, CESCO, Atlanta, Ga., USA) as means to determine glucose utilization by fungi. Additionally, final pH from all culture broths was recorded. All shake-flask culture experiments were run in duplicates and experiments were repeated at least three times on different dates.

We also sought to determine the effects of other culture conditions on blastospore production, desiccation tolerance, storage, and entomopathogenic capability. Among the parameters tested were osmotic pressure and increased aeration. To test for effects of variable osmotic pressure, cultures were grown in a basal salts medium with 2.5% cottonseed flour at 28° C., 350 rpm, and 50 mL in 250-mL baffled, Erlenmeyer flasks. Glucose concentrations from 20 g/L to 200 g/L were tested, as were glucose (10%) amended with 2%, 4% or 6% polyethylene glycol (PEG 200) and the non-toxic salts NaCl and KCl, both at 0.25 mol/L (14.32 g/L and 18.64 g/L, respectively).

To test for effects of varying amounts of aeration, liquid culture production of blastospores by various isolates of *B. bassiana* grown in a basal salts medium supplemented with 2.5% cottonseed flour (A) or acid hydrolyzed casein (B) and 10% glucose was analyzed. Fifty and 100 mL cultures were grown in 250 mL baffled, Erlenmeyer flasks in a shaker incubator at 28° C. and either 175 rpm or 350 rpm. Culture volumes were altered to increase (50 mL) or decrease (100 mL) aeration. Three-day-old blastospore suspensions were mixed with diatomaceous earth, filtered to remove spent media, and air-dried to <4% moisture. Blastospore viability was measured by evaluating germination after rehydrating and incubating air-dried blastospores in potato dextrose broth for 7 hours at 28° C. and 300 rpm in a shaker incubator.

Harvesting, Drying and Storage Studies

After growing *B. bassiana* and *I. fumosorosea* for 3 days, the whole culture was mixed with 7.5% (w/v) diatomaceous earth [DE (HYFLO®, Celite Corp., Lompoc, Calif., USA)]. The blastospore-DE mixtures were vacuum-filtered using a Buchner funnel with 12.5-cm filter paper disks (Whatman #1, Maidstone, England). The resulting filter cake from each replicate flask was crumbled, placed on 10-cm Petri dish, and air-dried overnight at ~22° C. in an air drying chamber with lateral air inflow (RH~50-60%) for 16-20 h to less than 4% moisture. Dried blastospore preparations were broken up by pulsing in a blender (Mini Prep® Plus, Cuisinart, East Windsor, N.J., USA), vacuum packaged (Multivac Inc., Kansas City, Mo., USA) in nylon polyethylene bags (15.3× 21.8 cm), and stored at 4° C. The moisture content (on wet basis [w.b.]) and water activity ($a_w$) of these formulations were measured before storage with a moisture analyzer (Mark II, Denver Instruments, Arvada, Colo., USA) and a water activity analyzer (AquaLab 4TEV, Decagon Devices, Inc., Pullman, Wash., USA), respectively, and considered as potential covariates.

At least 4 packages for each fungal isolate were obtained from different fermentation batches and monitored over time to assess the survivorship of air-dried blastospores. The viability of all air-dried blastospore preparations was determined immediately after drying and during storage using a previously described germination assay. Briefly, the germination assay was conducted by adding ~25 mg of air-dried blastospore preparation to 25 mL of potato dextrose broth [PD (Difco®)] in a 125-mL baffled Erlenmeyer flask. After 6 h incubation for *I. fumosorosea* and 7 h incubation for *B. bassiana* at 28° C. and 300 rpm in a rotary shaker incubator, percentage viability was determined microscopically by examining 200 discrete blastospores per replicate flask for germ tube formation. Germination was not assessed on clumps but rather where blastospores were discrete and were considered germinated when the germinating tube length was at least half of the blastospore diameter. Stability studies were conducted on samples stored under refrigerated conditions (4° C.) and blastospore viability monitored monthly over a period of 13 months using the described abovementioned germination protocol.

To determine the relationship between $a_w$ and moisture content, sorption isotherms were established for *B. bassiana* and *I. fumosorosea* formulated with 7.5% DE (w/v). Different saturated salt solutions were prepared to create different equilibrium relative humidities (ERH) using the following salts: sodium hydroxide (NaOH), lithium chloride (LiCl), magnesium chloride ($MgCl2.6H_2O$), potassium carbonate ($K_2CO_3$), sodium chloride (NaCl), potassium chloride (KCl), and potassium sulfate ($K_2SO_4$) that corresponded to aw values of 0.082, 0.113, 0.328, 0.432, 0.753, 0.843, and 0.973, respectively. All salts were purchased from Sigma®. To achieve very low ERH, Drierite® (anhydrous calcium sulfate, 8 mesh, W.A. Hammond Drierite Company, Xenia, Ohio, USA) was used as a standard desiccant agent and provided 0.0221 $a_w$. Salt solutions were added to the bottom of vacuum desiccators (206 mm height×149 mm inside diameter) (Bel-Art Products®, Wayne, N.J., USA), and samples were incubated 25° C. for seven days before readings.

Insects

The colony of *B. tabaci* biotype B was originally obtained from Apopka, Fla., USA, in 2013 and raised on cabbage cv. 'Bravo' (*Brassica oleracea* L.; Harris Seeds, Rochester, N.Y., USA) and blue lake bush bean (*Phaseolus vulgaris* L. [Kelly Seed Co., Peoria, Ill., USA]) with plants confined in 0.6 $m^3$ PVC-frame cages covered with fine screen fabric (off-white dracon chiffon material, BioQuip Products Inc., Rancho Dominguez, Calif., USA) under greenhouse conditions (temperature range: 24-30° C.). All plants were grown in a soil potting medium prepared with 77.5 L of pasteurized Redi Earth® growing mix (Sun Gro Horticulture Canada Ltd., Vancouver, Canada) amended with 60 g micromax granular and 400 g osmocote 14-14-14. Untreated seeds were used and plants were grown free of chemical pesticides.

Virulence of Fungal Spores Against Whitefly

To compare the virulence between blastospores and aerial conidia of *B. bassiana* and *I. fumosorosea*, insect bioassays were conducted against newly emerged second-instar *B. tabaci* biotype B nymphs, as described in previous studies. Laboratory bioassays were carried out with *B. bassiana* (ESALQ1432) and *I. fumosorosea* (CG1228). Blastospores were produced in a liquid culture medium, as previously described, containing 10% glucose and 2.5% cottonseed flour, and harvested after 3 days incubation at 28° C. and 350 rpm. Blastospore preparations (size range 3-11 µm) were formulated with 7.5% DE and air-dried to <4% moisture, while aerial conidia (size range 1.8-5.0 µm) were grown on PDA plates for 10-14 days at 22° C. and 12:12 (L:D) h photoperiod prior to use in bioassays. Original suspensions of both spores were prepared with a solution of Tween 80 at 0.01% and filtered once through a sterile double layer of cheesecloth. Desired concentrations were adjusted through serial dilutions using Tween 80 (0.01%) at $1\times10^5$, $5\times10^5$, $2.5\times10^6$, $1.25\times10^7$, and $6.25\times10^7$ spores/mL, which in turn corresponded to deposition rates (doses) of $1.26\times10^2$, $6.82\times10^2$, $3.7\times10^3$, $2.0\times10^4$, and $1.09\times10^5$ spores/$cm^{-2}$, respectively. Controls consisted of nymphs sprayed with 0.01% Tween 80 solution. The viability of blastospores used in all bioassays were >75% after 6 h (for *I. fumosorosea*) and 7 h (for *B. bassiana*) incubation in PD broth, while aerial conidia retained >90% viability after 17 h incubation on PDA at 25° C.

Individual bean leaves were placed in polystyrene Petri dishes (Falcon®, 100×15 mm) lined with 20 mL of water agar (2%, w/v), hereafter referred to as 'ventilated plates'. Each bean leaf, infested with 50-70 early second-instar nymphs, was sprayed with a micro-sprayer tower set to 10 PSI and 3 sec. There were five replicates per fungal-concentration and all concentrations were assayed at the same time. The entire experiment was repeated at least twice on different dates using different fungal batches and insect cohorts. After treatment, ventilated plates were inverted so that the abaxial side of the leaf faced down with the adaxial side touching the agar and then incubated in a growth chamber at 27±1° C., 70% (48-78%) RH and 14:10 (L:D) h photoperiod for six days before assessing mortality. Only nymphs showing signs of infection or symptoms from fungal disease (i.e., mycosis) were scored as dead individuals six days after application to estimate the median lethal concentration ($LC_{50}$), expressed as spores $cm^{-2}$. To compare the speed of kill between blastospores and aerial conidia, the same protocol previously mentioned was used, but at a concentration of $1.25\times10^7$ spores/mL (i.e., $2.7\times10^4$ spores/$cm^{-2}$), and mortality was recorded every 24 h after treatment over six days.

We also decided to compare, speed of kill and lethal dose of blastospores produced in media with low and high osmotic pressure to determine any effect. Blastospores of *B. bassiana* (ESALQ1432) were produced in liquid media with 2.5% cottonseed flour and glucose at 4%, 10%, or 14%. Blastospores were isolated as described above after 3 days growth. Blastospores were separated from culture broth with diatomaceous earth and air-dried. Exposure of whitefly nymphs (*B. tabaci* biotype B) is as described above.

Statistical Analysis

Experiments were carried out with a completely randomized design and repeated two to three times to ensure reproducibility. Generalized linear mixed models (GLMM) were used to fit data on blastospore counts with Poisson distribution and biomass accumulation with Gaussian (normal) distribution from the fermentation studies using the SAS macro PROC GLIMMIX. Fungal isolate, nitrogen source, and fermentation day (time) were implemented as fixed factors, while shake flasks (i.e., repeated measure over time) and experimental repetitions were declared as random effects in these models. Proportion data on blastospore viability from desiccation tolerance assays were fitted to a GLMM with binomial distribution for errors, in which experimental repetition was included in the random term, while fungal isolate and nitrogen source comprised the fixed factors. Statistics for fixed effects and their interaction terms were also determined by Wald type III F-test. Post-hoc pair-wise multiple comparisons were performed using Tukey's test at P≤0.05 for fixed effects and their interaction terms, once significance was detected. Time-course data on blastospore survival (% germination) at 4° C. storage were fitted to a logistic, 4-parameter nonlinear model to estimate the half-lives ($t_{1/2}$) of air-dried blastospores produced with different nitrogen sources. The model had the following notation: $S=S0+(\alpha/(1+(t/t0)\beta))$, where S is the blastospore survival (% germination), t is the storage time (in months) and $\alpha$, $\beta$ (slope), S0 and t0 are the best fit constants estimated by the interactive analysis performed in SAS macro PROC NLIN. To test the hypothesis that nitrogen source could affect the storage stability of air-dried blastospores across incubation time, the sum-of-squares reduction test was employed to compare their nonlinear regressions. The relationship between aw and moisture content for air-dried DE-formulated blastospores was explained by fitting the experimental results to the GAB (Guggenheim-Anderson-de Boer) model to draw the moisture sorption isotherm curves. We also tested whether the $a_w$ or moisture content could have any relation to the viability data for blastospores based on the Spearman's correlation (PROC CORR). Abbott's formula was applied to correct percentage mortality before estimating dose-response mortality relationships between different fungal spores and second-instar nymphs through a logistic model (PROC PROBIT). The logistic model was chosen as it provided the best fit due to its lowest deviance. Median lethal concentration ($LC_{50}$) with its corresponding confidence limits (95% CL), and slope were consecutively calculated for each spore type. Virulence of spore type was compared through the pair-wise ratio test at $\alpha=5\%$ applied to $LC_{50}$. Differences in speed of kill (median lethal time, $LT_{50}$) between blastospores and aerial conidia were analyzed using the previous logistic model to plot cumulative survival functions by treatment with pair-wise comparisons over the t-Student test at $P\leq0.05$. All analyses were performed in the Statistical Analysis System v.9.2 (SAS Institute Inc., Cary, N.C.).

Experimental Results

Blastospore Yield and Biomass Accumulation

Fungal isolates responded significantly different in terms of filamentous growth when cultured in liquid media supplemented with different sources of nitrogen (FIG. 1—results shown for two B. bassiana isolates). In general, the results demonstrate that B. bassiana isolates grow in a yeast-like form with improved blastospore yield when the nitrogen source is cottonseed flour, soy flour, autolyzed yeast or acid hydrolysed casein (AHC). Additionally, most of the nitrogen sources resulted in an adequate level of desiccation tolerance. Similar results were obtained for I. fumosorosea (data not shown). Two of these nitrogen sources (AHC and cottonseed flour) were chosen as the nitrogen sources for further experiments.

Liquid cultures supplemented with AHC or cottonseed flour at 25 g/L were grown as described above and their growth parameters analyzed. Based on daily observations, there was a significant increase in blastospore yield as well as in biomass accumulation from day 2 to day 3 of growth for all isolates of B. bassiana and I. fumosorosea, regardless of the nitrogen source (Tables 2, 3—lowercase letters refer to comparison between fungal isolates and nitrogen sources within each fermentation day (in columns), while uppercase letters refer to comparisons between fermentation day (in rows) for each isolate.).

TABLE 2

Liquid culture productivity of B. bassiana strains

| B. bassiana strain | Nitrogen source | Biomass (mg/mL) | | Yield ($\times 10^8$ blastospores/mL) | |
|---|---|---|---|---|---|
| | | Day 2 | Day 3 | Day 2 | Day 3 |
| CG1229 | AHC | 11.7 ± 0.6 b, B[†] | 15.3 ± 0.2 e, A | 3.4 ± 1.3 c, B | 5.5 ± 1.4 b, A |
| | Cottonseed flour | 25.1 ± 0.5 a, A | 26.0 ± 0.7 bc, A | 8.8 ± 1.8 ab, A | 9.11 ± 1.2 ab, A |
| ESALQ1432 | AHC | 12.9 ± 1.7 b, B | 20.5 ± 0.7 d, A | 4.4 ± 0.3 bc, B | 7.9 ± 0.8 ab, A |
| | Cottonseed flour | 28.5 ± 1.9 a, B | 32.8 ± 0.3 a, A | 8.3 ± 0.5 ab, B | 12.4 ± 1.0 a, A |
| ESALQ447 | AHC | 12.9 ± 0.9 b, B | 16.4 ± 0.5 e, A | 2.4 ± 0.2 c, B | 6.8 ± 0.8 ab, A |
| | Cottonseed flour | 26.1 ± 1.6 a, A | 24.2 ± 0.9 c, A | 5.1 ± 0.4 abc, B | 7.8 ± 0.5 ab, A |
| ESALQ-PL63 | AHC | 14.3 ± 0.9 b, A | 15.5 ± 0.3 e, A | 0.34 ± 0.06 d, B | 0.95 ± 0.1 c, A |
| | Cottonseed flour | 25.9 ± 0.9 a, A | 24.0 ± 0.6 c, A | 0.30 ± 0.02 d, B | 1.2 ± 0.1 c, A |
| GHA | AHC | 10.5 ± 0.4 b, B | 16.2 ± 0.5 e, A | 2.7 ± 0.5 c, B | 4.9 ± 0.5 b, A |
| | Cottonseed flour | 25.9 ± 0.7 a, A | 28.0 ± 1.8 b, A | 10.0 ± 0.6 a, A | 11.6 ± 0.6 a, A |

TABLE 3

Liquid culture productivity of I. fumosorosea strains

| I. fumosorosea strain | Nitrogen source | Biomass (mg mL$^{-1}$) | | Yield ($\times 10^8$ blastospores mL$^{-1}$) | |
|---|---|---|---|---|---|
| | | Day 2 | Day 3 | Day 2 | Day 3 |
| CG1228 | AHC | 22.1 ± 1.5 a, B | 33.3 ± 2.8 a, A | 14.4 ± 1.7 ab, B | 26.0 ± 0.9 ab, A |
| | Cottonseed flour | 31.8 ± 1.5 a, B | 40.9 ± 1.1 a, A | 15.4 ± 1.5 a, B | 27.9 ± 2.2 a, A |
| ESALQ 1296 | AHC | 21.7 ± 0.5 a, B | 34.6 ± 2.0 a, A | 9.6 ± 1.1 abc, B | 16.6 ± 0.7 bc, A |
| | Cottonseed flour | 30.6 ± 1.5 a, B | 40.6 ± 2.2 a, A | 10.0 ± 0.9 abc, A | 13.0 ± 1.1 c, A |
| ESALQ 1364 | AHC | 20.5 ± 1.2 a, B | 32.2 ± 2.5 a, A | 9.6 ± 0.5 abc, B | 15.3 ± 1.7 c, A |
| | Cottonseed flour | 29.1 ± 0.7 a, B | 36.9 ± 0.5 a, A | 6.7 ± 0.6 b, A | 6.9 ± 0.9 d, A |
| ESALQ 1409 | AHC | 20.4 ± 1.4 a, B | 33.2 ± 2.6 a, A | 8.7 ± 0.6 abc, B | 13.8 ± 1.9 c, A |
| | Cottonseed flour | 31.6 ± 0.8 a, B | 38.7 ± 1.8 a, A | 9.4 ± 0.3 abc, B | 15.3 ± 1.5 c, A |
| ARSEF 3581 | AHC | 23.7 ± 1.0 a, B | 33.9 ± 2.1, A | 11.2 ± 2.4 abc, A | 14.3 ± 1.4 c, A |
| | Cottonseed flour | 31.2 ± 1.5 a, B | 37.6 ± 1.4, A | 8.9 ± 1.9 bc, A | 10.4 ± 1.5 cd, A |

Isolates of B. bassiana exhibited different growth rates measured as blasto spore concentration over time, as the interaction term between isolate and fermentation day was significant ($F_{4,105}=5.97$, $P=0.0002$), whereas blastospore production increased at the same rate for I. fumosorosea isolates over time ($F_{4,62}=2.28$, $P=0.0708$). Blastospore counts usually reached higher numbers by day 3 growth for both *B. bassiana* (F1,105=71.89, P=0.0001) and *I. fumosorosea* (F1,62=53.29, P<0.0001), although some isolates did not produce significantly more blastospores by day 3 compared with day 2. Fungal isolate and nitrogen source interaction had a strong impact on blastospore yields for *I. fumosorosea* (F4,62=5.53, P=0.0007), but only a spurious effect for B *bassiana* (F4,105=2.42, P=0.0531). The effect of nitrogen source by itself was more pronounced on blastospore production for *B. bassiana* (F1,105=16.97, P<0.0001), whose isolates attained higher concentrations when grown with cottonseed flour, except for isolate ESALQ-PL63 which was not responsive. The opposite outcome was observed for isolates ESALQ1364 and ARSERF3581 of *I. fumosorosea* that yielded higher blastospore counts when cultured with acid hydrolyzed casein rather than cottonseed flour (F1,62=13.61, P=0.0005), although the other isolates did not respond differently to the nitrogen sources. Comparisons among *Isaria* isolates revealed that CG1228 attained the highest concentration of blastospores (2.6-2.8×10$^9$ blastospores/mL) at day 3, regardless of the nitrogen source (F4,62=37.04, P<0.0001). Under the same fermentation conditions, the best blastospore-producing isolates of *B. bassiana* were CG1229, GHA and ESALQ1432 grown in liquid media with cottonseed flour rather than acid hydrolyzed casein attaining yields of 0.9-1.2×10$^9$ blastospores/mL in 3 days of growth (F4,105=21.2, P<0.0001). It is interesting to note that all isolates of *I. fumosorosea* were able to produce more than 1×10$^9$ blastospores/mL by day 3, whereas only ⅔ of the *B. bassiana* isolates reached this high spore concentration. In addition, *I. fumosorosea* isolates demonstrated a faster filamentous growth compared to *B. bassiana* isolates. Among all fungal isolates tested, ESALQ-PL63 showed the poorest yeast-like growth by growing more hyphally, which resulted in a thick, viscous culture broth.

Figure 2:
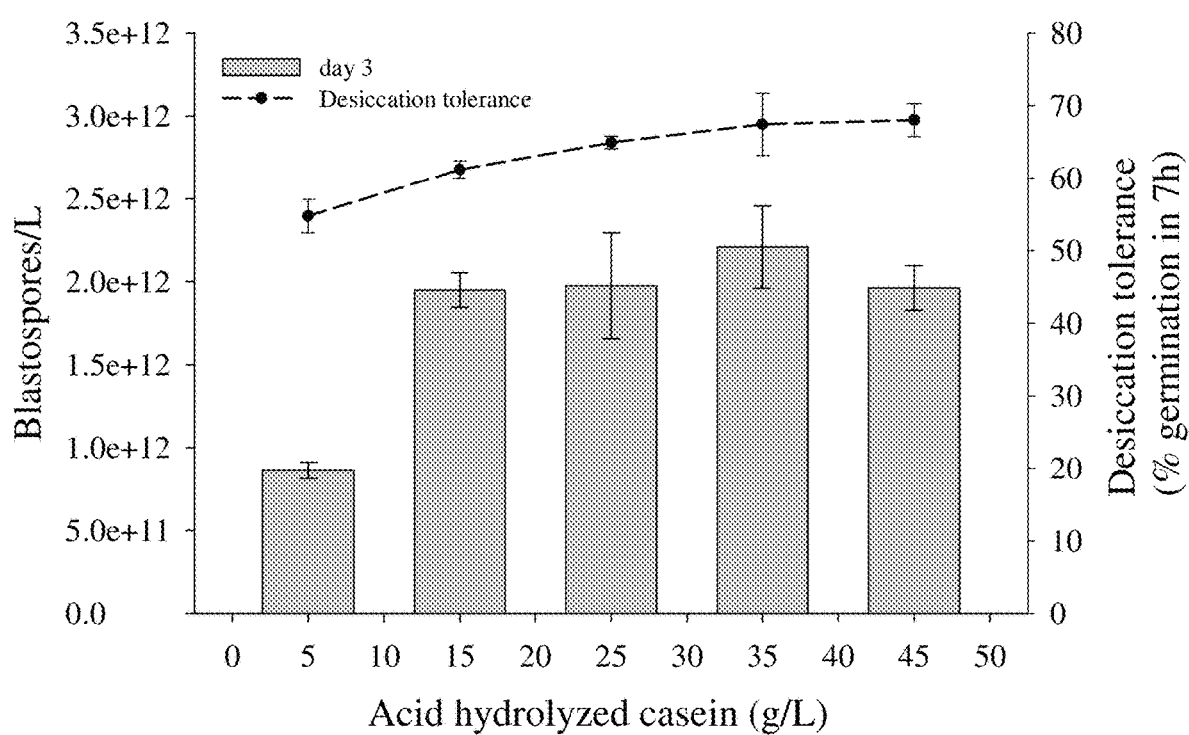
FIG. 2 provides a graphic representation of increased blastospore yield and desiccation tolerance when grown in the presence of increasing levels of nitrogen.

With respect to the biomass accumulation, data were examined separately for each nitrogen source, since media amended with cottonseed flour contained previously higher amount of solids (15.54±0.08 mg/mL) compared with acid hydrolyzed casein (0.07±0.01 mg/mL), making comparisons difficult. Irrespective to the nitrogen source, dry biomass did not vary among *I. fumosorosea* isolates (F4,62=1.81, P=0.1383), although most of these isolates increased biomass over time (F1,62=20.43, P<0.0001) (Tables 2, 3). When growing *B. bassiana* isolates in media supplemented with acid hydrolyzed casein, culture dry weight increased considerably over time in relation to cottonseed flour (F4, 105=7.77, P<0.0001). Both *B. bassiana* and *I. fumosorosea* accumulated more dry weights by day 3 (F1,105=43.77, P<0.0001; F1,62=583.36, P<0.0001, respectively). Apart from the nitrogen source, ESALQ1432 of *B. bassiana* showed the highest biomass among all the isolates (F4, 105=15.04, P<0.0001). Finally, the final pH of *B. bassiana* and *I. fumosorosea* cultures after fermentation had increased acidity and were very similar with pH ranging from 3.8-4.8 and 3.6-4.9, respectively. Blastospore production and desiccation tolerance increased with increasing concentration of nitrogen source, possibly plateauing at higher levels (FIG. 2).

Desiccation Tolerance

Drying 3-day-old blastospores to <4% moisture content ($a_w$<0.3) revealed a significant interaction effect between nitrogen source and fungal isolate on blastospore viability for *I. fumosorosea* (F4,29=4.90, P=0.0038) and *B. bassiana* (F4,56=5.26, P=0.0011). Desiccation tolerance was assessed by measuring germination by air-dried blastospores rehydrated in potato dextrose broth (PD) and incubated for 7 hours and 6 hours at 28° C. and 300 rpm for *B. bassiana* and *I. fumosorosea* respectively. When examining viability within *B. bassiana*, blastospores from isolates ESALQ1432 and ESALQ447 were more desiccation tolerant with greater spore viability (71-79%) when produced with cottonseed flour than acid hydrolyzed casein (F1,56=14.06, P=0.0004) (Table 4—non-corresponding letters denote statistical differences with small letters referring to comparison between isolates within each nitrogen source (columns), while uppercase letters refer to comparisons between nitrogen sources (rows) for each isolate).

TABLE 4

Desiccation tolerance in *B. bassiana* and *I. fumosorosea* blastospores

| | Desiccation tolerance (% Blastospore survival)* | |
|---|---|---|
| Fungal isolates | Acid hydrolyzed casein | Cottonseed flour |
| *Beauveria bassiana* | | |
| CG1229 | 80.8 ± 2.1 a, A | 78.2 ± 2.3 c, A |
| ESALQ1432 | 73.0 ± 2.8 b, B | 79.2 ± 2.4 bc, A |
| ESALQ447 | 73.9 ± 2.7 b, B | 84.0 ± 2.0 ab, A |
| ESALQ-PL63 | 85.3 ± 2.0 a, A | 86.5 ± 1.9 a, A |
| GHA | 70.9 ± 3.0 b, A | 75.5 ± 2.8 c, A |
| *Isaria fumosorosea* | | |
| CG1228 | 80.3 ± 2.5 a, A | 74.1 ± 2.9 ab, B |
| ESALQ1296 | 77.3 ± 2.7 a, A | 68.6 ± 3.1 b, B |
| ESALQ1364 | 74.1 ± 2.9 ab, A | 65.3 ± 3.3 b, B |
| ESALQ1409 | 62.3 ± 3.4 b, B | 70.6 ± 3.1 ab, A |
| ARSEF3581 | 82.4 ± 2.4 a, A | 79.1 ± 2.6 a, A |

By contrast, *I. fumosorosea* isolates showed better desiccation tolerance with greater spore viability when grown in media containing acid hydrolyzed casein rather than cottonseed flour (F1,29=8.37, P=0.0072), expect for isolates ESALQ1409 and ARSEF3581. Blastospore survival after air-drying significantly varied across isolates within *B. bassiana* (F4,56=16.5, P<0.0001) and *I. fumosorosea* (F4, 29=12.96, P<0.0001). Analysis within *B. bassiana* indicated that both nitrogen sources supported higher initial viability rates (70-86%) after air-drying, while *I. fumosorosea* isolates attained an initial survival of 62-82% of blastospores.

Figure 3:
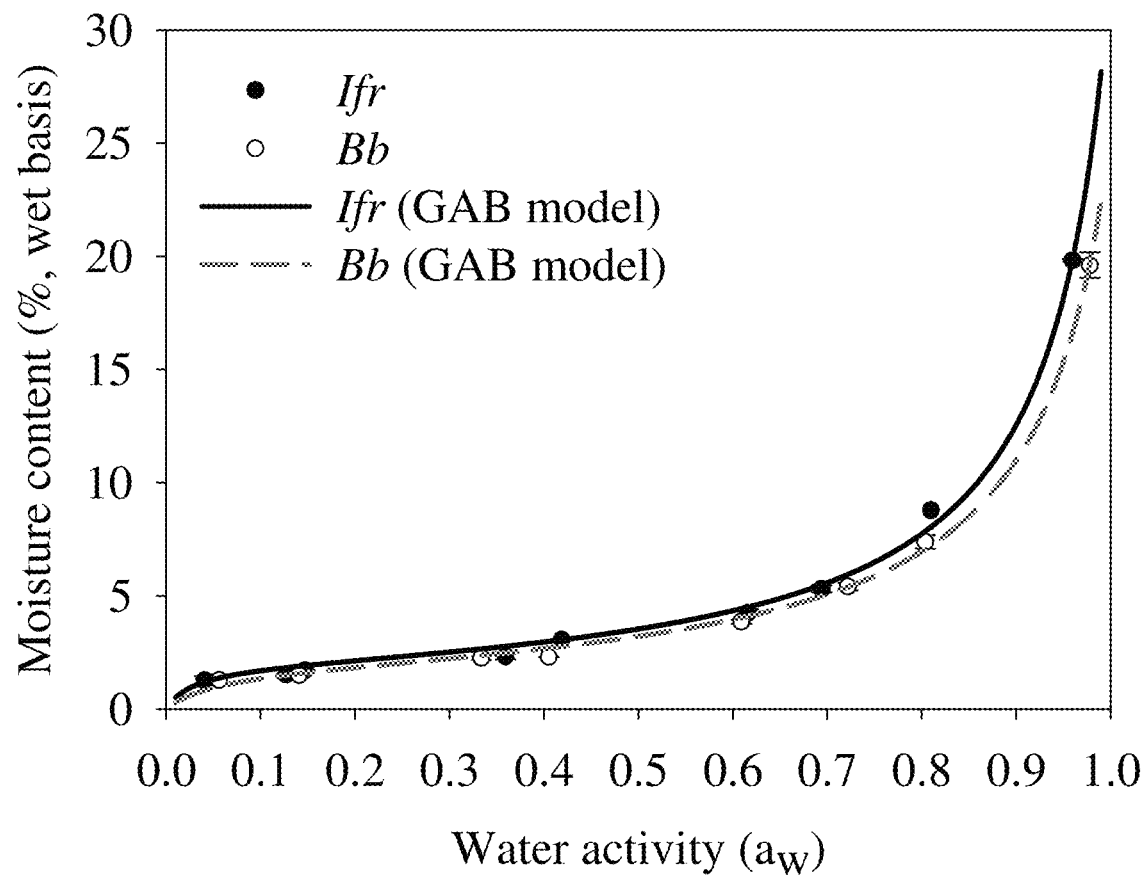
FIG. 3 provides a graph showing the relationship between water activity ($a_w$) and moisture content in air-dried blastospores of two fungal genera.

After air-drying, the moisture sorption isotherms were determined at 25° C. to describe the relationship between aw of fungal biomass (blastospores+mycelium) formulated with 7.5% DE and moisture content (%, wet weight basis). Experimental data were significantly explained by the GAB model (*B. bassiana*: R2=0.99, F3,28=3666.55, P<0.0001; *I. fumosorosea*: R2=1.00, F3,21=2738.01, P<0.0001) assuming a sigmoidal shape curve (FIG. 3). Water activities ($a_w$) of air-dried blastospores of *B. bassiana* isolates ranged from 0.251-0.364 with corresponding moisture contents of 1.38-2.70%, while for *I. fumosorosea* isolates aw varied from 0.270-0.323 that corresponded to 1.76-2.63% water content. Neither water activity nor moisture content was correlated with initial blastospore survival rates after drying for either fungal species (Spearman correlation: −0.02≤r≤0.30, 0.06≤P≤0.86). Blastospores of *B. bassiana* grown under conditions described herein survive spray-drying (mixed with skim milk powder (SMP) or SMP+2.5% ascorbic acid) and air-drying (mixed with diatomaceous earth) equally well. These results are reported in Table 5, there was no significant difference regardless of formulation or drying process. Desiccation tolerance was measured as the percent blastospores germinated upon rehydration in PD broth after 7 hours incubation at 28° C. and 300 rpm.

TABLE 5

Air-drying and spray-drying *B. bassiana* blastospores

| Dehydration method | Formulation | Moisture (%) | Water activity | Desiccation tolerance (% germination)[b] |
|---|---|---|---|---|
| Spray drying | 20% SMP | 4.48 (2.85-5.79) | 0.195 (0.077-0.2827) | 83.1 ± 1.2 |
| | 17.5% SMP + 2.5% Ascorbic Acid | 4.47 (3.84-5.75) | 0.253 (0.184-0.324) | 82.6 ± 0.7 |
| Air drying | Diatomaceous earth | 0.84 (0.56-1.31) | 0.246 (0.2142-0.2876) | 80.9 ± 1.0 |

Storage

Figure 4:
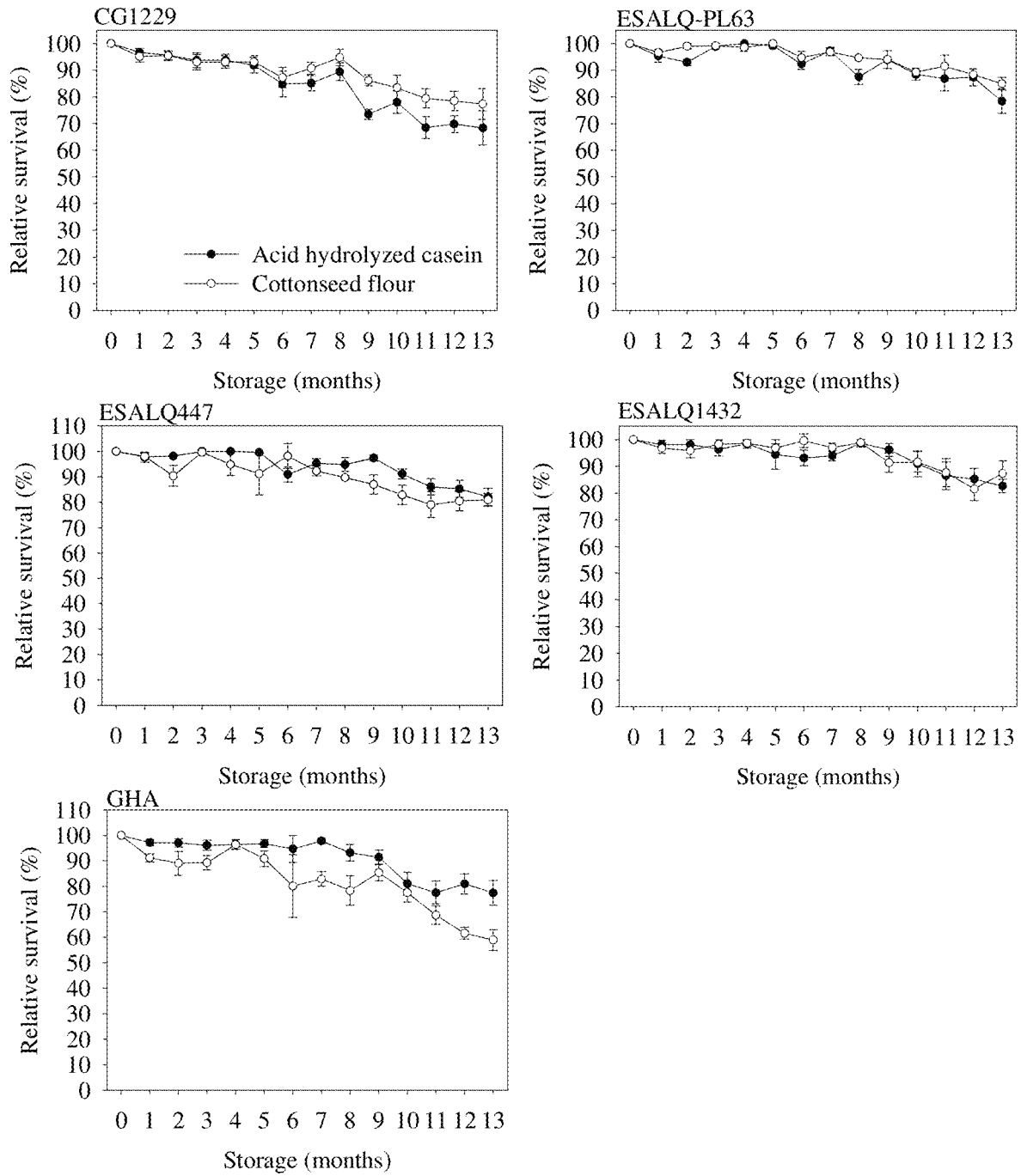
FIG. 4 provides graphs demonstrating long-term survival rates for several *B. bassiana* strains stored at 4° C.
Figure 5:
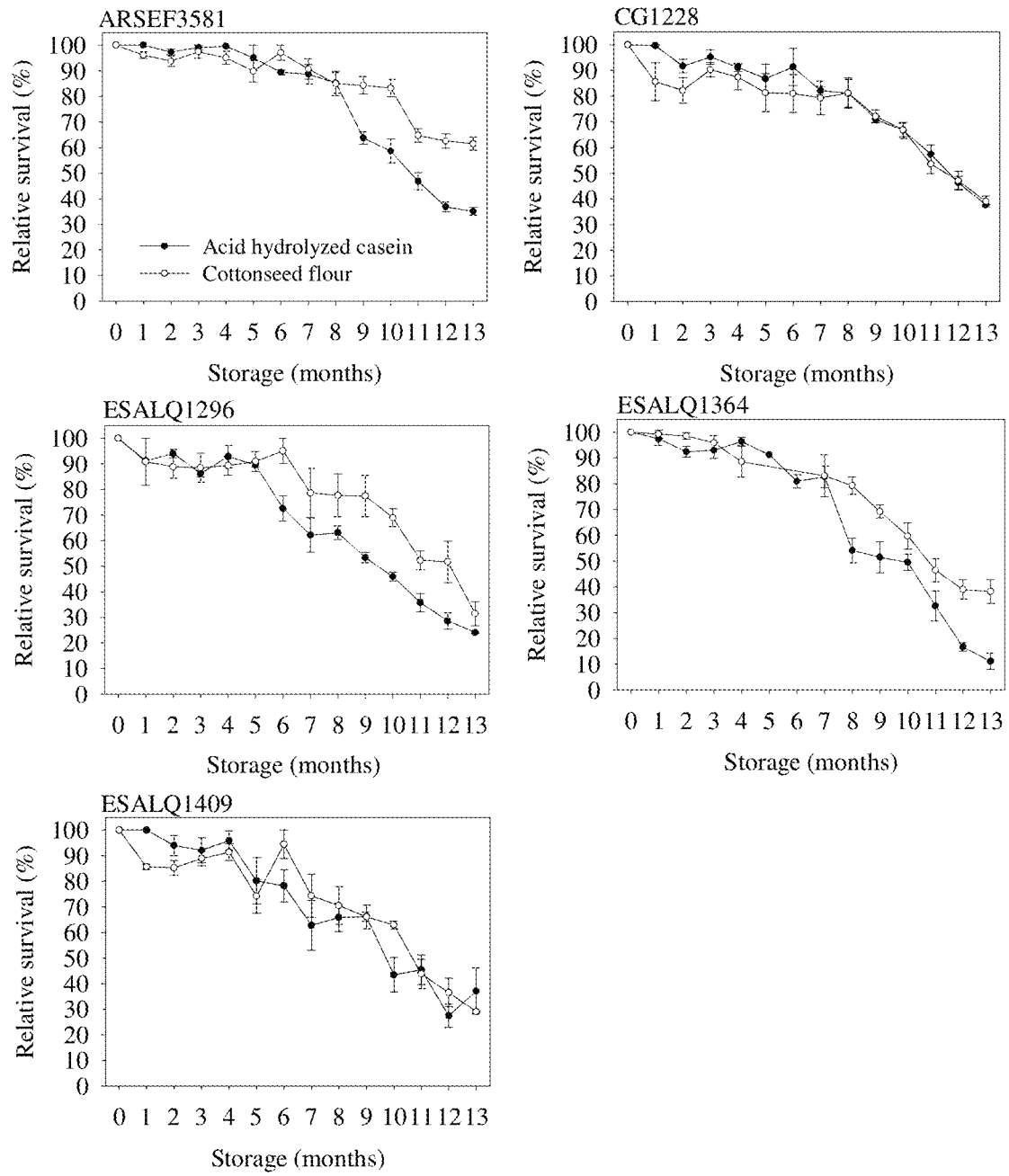
FIG. 5 provides graphs demonstrating long-term survival rates for several *I. fumosorosea* strains stored at 4° C.

The long-term storage stability of air-dried blasto spores under refrigerated conditions varied with the fungal isolate and nitrogen source (FIGS. 4, 5). The logistic model with four parameters fitted well (R2=0.74-0.99, P<0.01) the experimental data on blastospore survival across storage time for all isolates of *B. bassiana* and *I. fumosorosea* produced with either nitrogen source. According to the sum-of-squares reduction test used to compare the nonlinear regressions for blastospore survival curves, it was found that the nitrogen source did not influence the survivorship of air-dried blastospores of *B. bassiana* over the period of 13 months of cool storage, except the isolates CG1229 and GHA that survived considerably longer when produced with cottonseed flour and acid hydrolyzed casein, respectively (FIG. 4). Particular to *I. fumosorosea*, blastospores of isolates ARSEF3581, ESALQ1296, and ESALQ1364 retained higher viability for a longer period of time when grown in cottonseed flour, whereas the long-term viability of the other isolates was not influenced by the nitrogen source (FIG. 5). Generally, survival curves of *I. fumosorosea* blastospores depicted a faster decay pattern compare with *B. bassiana*, regardless of the nitrogen source. Estimates of half-lives for *B. bassiana* air-dried blastospores stored at 4° C. exhibited a minimum time of 14.1 months for GHA grown in cottonseed flour, while most isolates retained a half-life longer than 14 months (Table 5). By contrast, *I. fumosorosea* air-dried blastospores showed the shortest half-life (9.2 months) with ESALQ1296 grown in acid hydrolyzed casein. The longest half-life achieved by *I. fumosorosea* (13.1 months) was ARSEF3581 grown in cottonseed flour. In most cases, cottonseed flour supported longer half-lives for *I. fumosorosea* isolates.

We also tested a variety of packaging and storage options for insecticidal compositions of the present invention, specifically testing for storage conditions that favored long-term storage at "high room temperature" (28° C.). For the results shown in Table 6, half-life was calculated as ln(2)/b. All vacuum packaging was at 999 mbar pressure, providing ≤0.021% atmospheric oxygen in aluminum (mylar) bags. Silica gel (SG) was used as a moisture absorber. ZM-1 and ZPT-50 were used as oxygen scavengers separately. RP-3A is a combination oxygen scavenger and moisture scavenger.

TABLE 6

High room temperature storage effects with variable packaging.

| Drying method | Formulation | Packaging | Storage temperature (° C.) | $t_{1/2}$ (weeks) |
|---|---|---|---|---|
| Spray drying | SMP | Vacuum sealed | 28 | 2.0 |
| | | | 4 | >36 |
| Air drying | DE | Vacuum sealed | 28 | 13.3 |
| | | | 4 | >36 |
| Spray drying | SMP | Control | 28 | 2.3 |
| | | RP-3A | 28 | 31.5 |
| | | SG | 28 | 2.4 |
| | SMP + ASA | Control | 28 | 2.4 |
| | | RP-3A | 28 | 59.2 |
| | | ZM-1 | 28 | 2.0 |
| | | ZPT-50 | 28 | 1.6 |
| | | SG | 28 | 3.0 |
| Spray drying | SMP | Control | 28 | 2.0 |
| | | ZM-1 + SG | 28 | 5.0 |
| | | ZPT-50 + SG | 28 | 3.2 |
| | | ZM-1 | 28 | 3.5 |
| | | ZPT-50 | 28 | 1.8 |
| | | SG | 28 | 2.4 |
| Air drying | DE | Control | 28 | 3.0 |
| | | RP-3A | 28 | >36 |
| | | ZM-1 | 28 | 3.2 |
| | | ZPT-50 | 28 | 1.3 |
| | | SG | 28 | 16.1 |

To further investigate the differences seen between storage methods, we analyzed the different oxygen and moisture scavengers.

Figure 6:
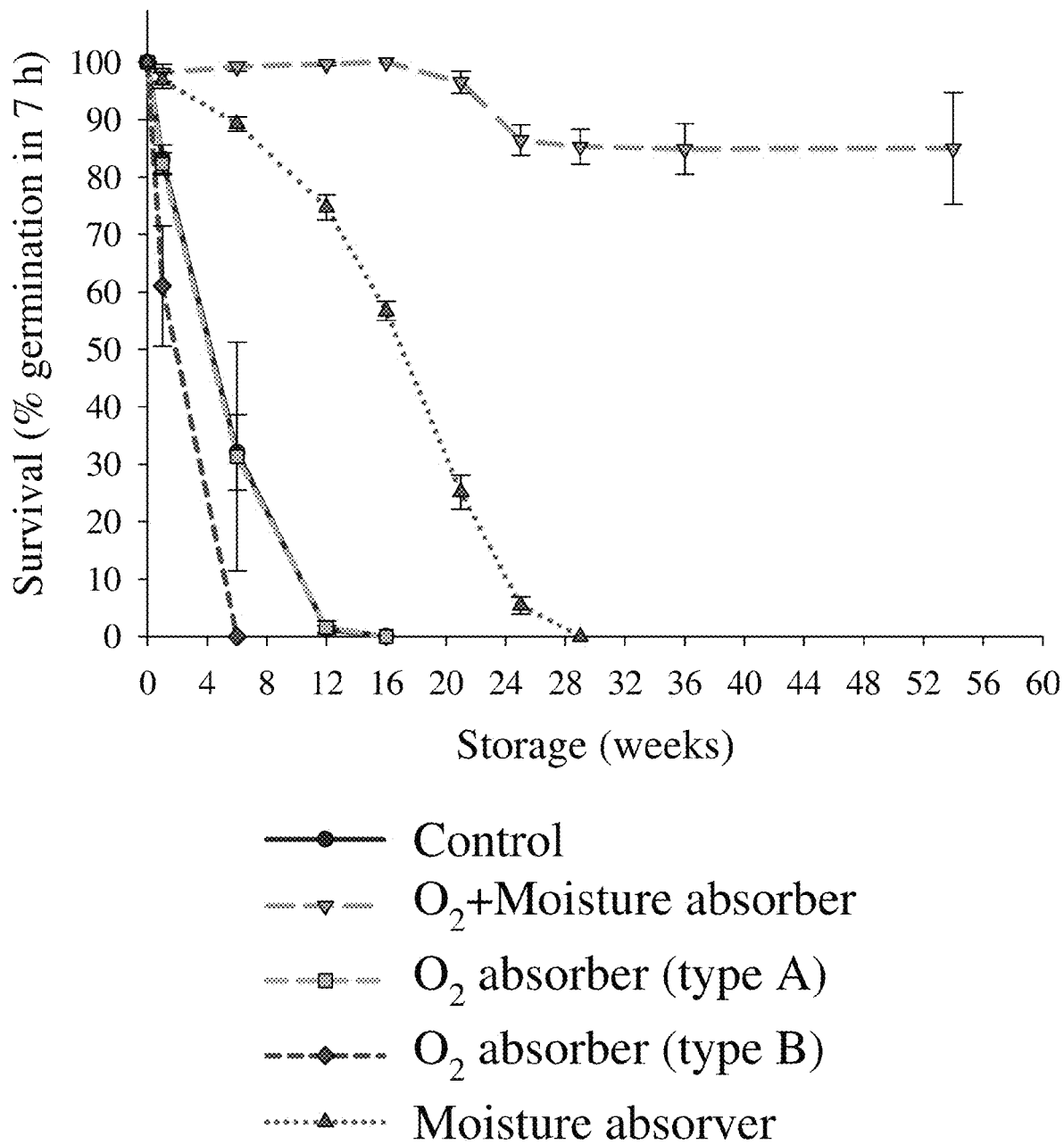
FIG. 6 provides a graph showing *B. bassiana* blastospore survival rates at 28° C. in the presence of oxygen and moisture scavengers.
Figure 7:
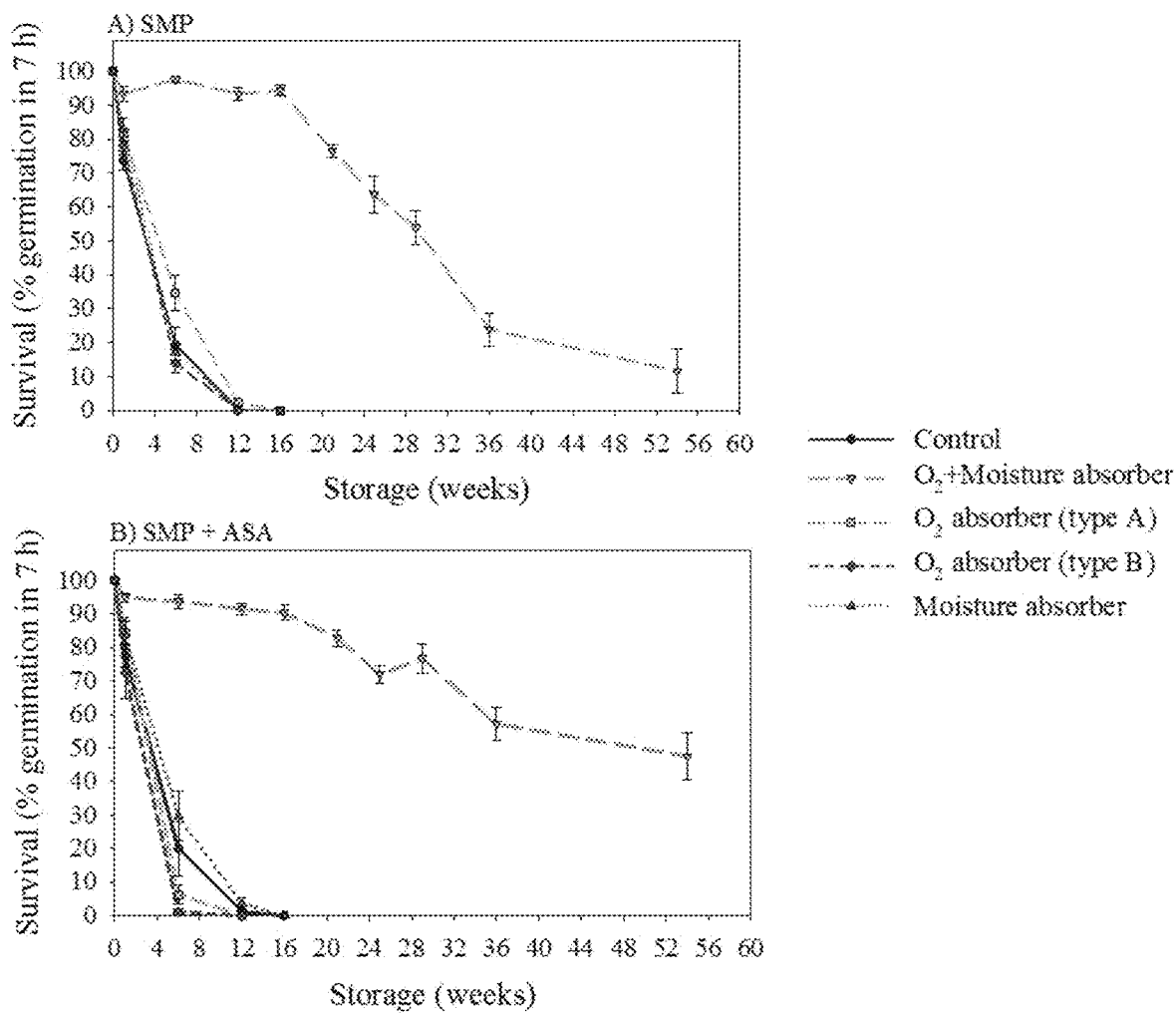
FIG. 7 provides a graph showing *B. bassiana* blastospore survival rates in the presence of oxygen and moisture scavengers. Cells were spray-dried with or without ascorbic acid (ASA).

Effect of oxygen and moisture scavengers on the storage stability of air dried *Beauveria bassiana* blastospores stored at 28° C. was measured with each of the above packaging combinations. Results are shown in FIG. 6 (RP-3A="$O_2$+Moisture absorber"; ZM-1="$O_2$ absorber type A"; ZPT-50="$O_2$ absorber type A"; Silica gel="Moisture absorber") Survivorship was reported as the percentage of viable spores remaining relative to freshly dried blastospore samples. Germination was measured as germ tube elongation after 7 hrs incubation in potato dextrose broth, 28 C, and 300 rpm agitation. Results of a similar analysis for *B. bassiana* blastospores spray dried with SMP (with and without ascorbic acid (ASA) show that addition of ASA to the formulation increases survival of spray-dried formulations (FIG. 7).

Osmotic Pressure

Figure 8:
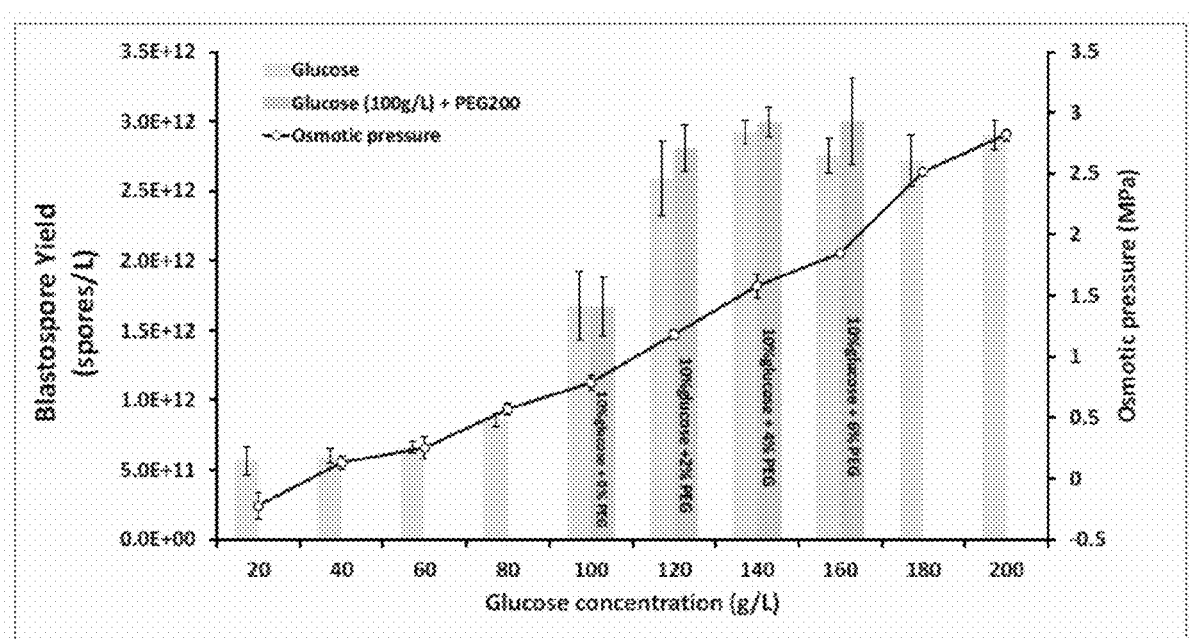
FIG. 8 provides a graph showing blastospore production rate for cultures of *B. bassiana* ESALQ1432 at different glucose concentrations and osmotic pressure points.
Figure 9:
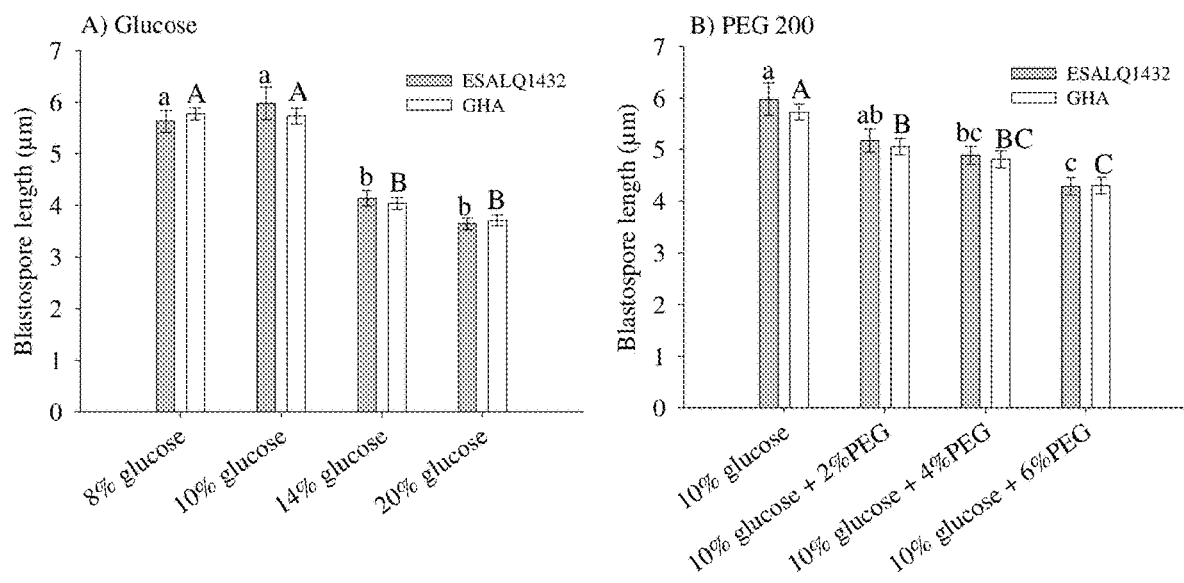
FIG. 9 provides morpohological analysis of blastospores grown in the presence of increased osmotic pressure.

Our results show that increased osmotic pressure resulted in an increased blastospore yield which was not simply due to increased availability of glucose to the yeast-like cells (FIG. 8, Table 7—Means (±SE) followed by different letters are significantly different (Tukey test, P<0.05). For the osmolytes listed in Table 7, the listed concentrations are equivalent to 200, 14.32 and 18.64 g/L for glucose, NaCl and KCl, respectively. Media containing the NaCl and KCl amendments contained 100 g glucose (0.56M) as a source of carbon.). Lowercase letters refer to comparisons within strain for each sample day (columns), while uppercase letters refer to comparisons across fermentation day within strain (rows)). Blastospores of the invention produced under high osmotic pressure (>0.5 MPa) exhibited a spherical morphology that is smaller and unlike oblong blastospores produced in typical growth media (FIG. 9). This spherical shape of the blastospores is associated with greater infectivity of targeted pests and represents a unique blastospore form that has not been previously reported (see below).

TABLE 7

Increased blastospore production induced by increased osmotic pressure

| B. bassiana strain | Osmolyte (mol/L) | Osmotic pressure (MPa) | Blastospores concentration ($\times 10^8$ mL$^{-1}$) Day 2 | Day 3 | Desiccation tolerance (% germination) |
|---|---|---|---|---|---|
| ESALQ1432 | Glucose (1.1) | 2.7 | 17.3 ± 1.2 aB | 29.0 ± 1.1 aA | 66.2 ± 2.1 |
|  | NaCl (0.25) | 2.5 | 12.1 ± 0.8 bB | 33.1 ± 1.4 aA | 76.1 ± 2.8 |
|  | KCl (0.25) | 2.5 | 11.1 ± 1.2 bB | 29.6 ± 1.8 aA | 70.7 ± 2.0 |
| GHA | Glucose (1.1) | 2.7 | 15.6 ± 1.2 aB | 29.4 ± 2.0 aA | 58.6 ± 2.2 |
|  | NaCl (0.25) | 2.5 | 12.7 ± 0.5 aB | 24.1 ± 1.7 aA | 57.4 ± 1.1 |
|  | KCl (0.25) | 2.5 | 15.1 ± 0.9 aB | 26.1 ± 1.9 abA | 54.2 ± 1.4 |

High Aeration

Although previous studies have indicated that higher aeration rates obtained by using baffled flasks and higher agitation provide more oxygen to liquid cultures and enhanced blastospore yields of *I. fumosorosea*, there has been the counter teaching that there is no increase in spore production of *B. bassiana* above 200 rpm (Pham et al., Mycobiology 2009).

Figure 10:
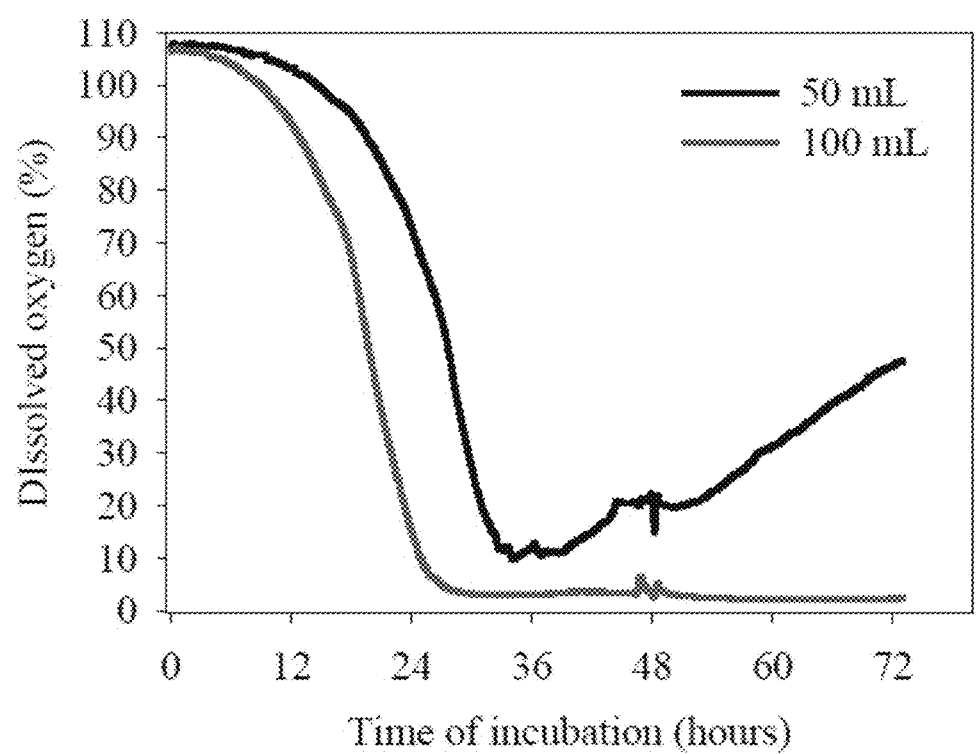
FIG. 10 provides a graph showing dissolved oxygen levels are affected by culture volume.

Initial results suggest that it is the volume of culture that is important. When we compared 50 mL cultures with 100 mL cultures (basal salt medium, 2.5% cottonseed flour, 10% glucose in 250 mL baffled Erlenmeyer flasks, 28° C. and 350 rpm), we noted that dissolved oxygen levels were higher in the smaller volume (FIG. 10). We also tested varying agitation speed, discovering that higher speeds increased blastospore production in both 50 and 100 mL cultures (Table 8—for each strain and each sample day, mean values followed by the different letters are significantly different (Tukey test, P<0.05).). Production of high yields of blastospores of *B. bassiana* using deep tank fermentation further supports the requirement for elevated dissolved oxygen levels (data not shown).

TABLE 8

Effects of higher aeration on blastospore yield

| Beauveria bassiana Strain | Agitation speed (RPM) | Medium volume (mL) | Blastospore Production (blastospores L$^{-1}$ × 10$^{11}$) Day 2 | Day 3 |
|---|---|---|---|---|
| ESALQ1432 | 350 | 100 | 7.6 ± 1.0 b† | 9.9 ± 1.1 a |
|  |  | 50 | 11.0 ± 0.6 a | 14.0 ± 1.5 b |
|  | 175 | 100 | 3.3 ± 0.1 c | 3.3 ± 0.3 c |
|  |  | 50 | 4.9 ± 0.2 c | 5.7 ± 0.5 c |

Figure 11:
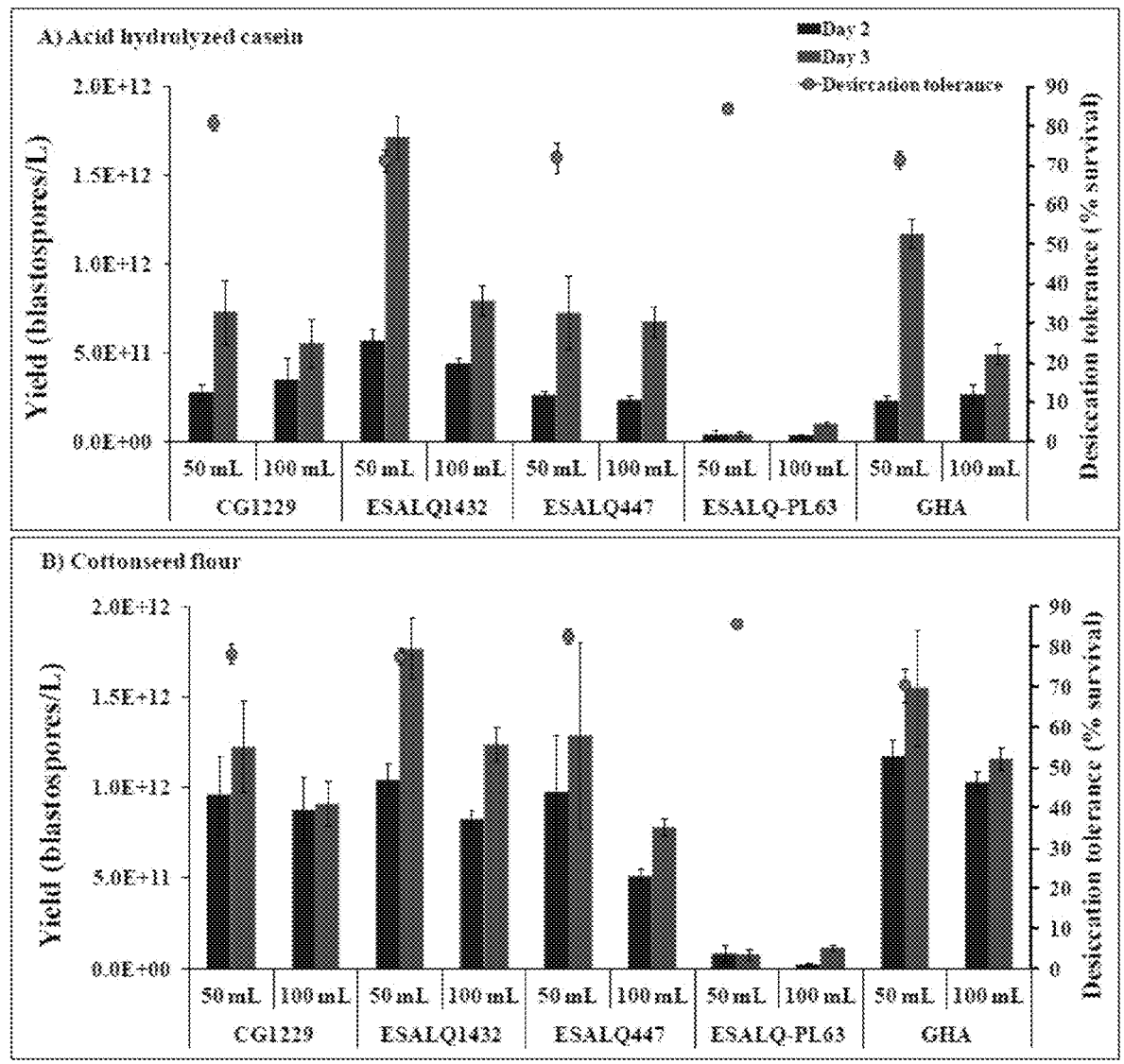
FIG. 11 provides two panels showing blastospore yield and desiccation tolerance in cultures of varying volumes and different nitrogen sources.

The results demonstrate that *B. bassiana*, as well as *I. fumosorosea* (data not shown), cultures grown under highly aerated conditions (dissolved oxygen level above zero for most of the fermentation) with appropriate concentrations of a nitrogen source (>15 g/L), carbon source (≥60 g/L), and osmotic pressure greater than 0.5 MPa achieved rapid production of high numbers of blastospores (FIG. 11). Blastospores produced under these conditions provide a feasible production and stabilization process for *Beauveria* blastospores using inexpensive media components. Previous attempts in producing *Beauveria* blastospores using liquid culture fermentation processes required longer fermentation times (6-8 days) to maximize yields and produced cells that had poor survival after desiccation and storage.

Efficacy Against Whitefly

To compare the virulence between blastospores and aerial conidia, we bioassayed second-instar *B. tabaci* biotype B nymphs. Virulence tests revealed that blastospores of *B. bassiana* required four-fold lower spore concentration to kill 50% of nymphs than aerial conidia (Table 9). A total of ten (10) replications, each containing more than fifty (50) whitefly nymphs were tested per fungal concentration. The delivered median lethal concentration (LC$_{50}$) is expressed in propagules/cm$^2$ and estimated by the logistic model. Cumulative mortality censored up to day 6 post-application. Control mortality averaged 3.7±1.3%. Relative potency is the measure of relative efficacy of blastospores to aerial conidia within each fungal species: (LC$_{50}$ conidia/LC$_{50}$ blastospores). Comparisons were undertaken within each fungal species and if the confidence limit for the LC ratio does not contain 1, thereby it is concluded that the LC values are significantly different. $\chi^2$ and P values represent the probability of slope≠0, rather than fit to logistic model.

TABLE 9

B. bassiana blastospores are more effective than conidia for whitefly control

| Spore type | $n^a$ | LC$_{50}$ (propagules/cm$^2$)$^b$ | (95% CL)$^c$ Lower | Upper | RP$_{50}^d$ | (95% CL) Lower | Upper | $\chi^2$ (P-value)$^e$ |
|---|---|---|---|---|---|---|---|---|
| Blastospores | 3113 | 485 | 353 | 643 | 4.6 | 3.25 | 6.50 | 109.35 (<0.0001) |
| Conidia | 3059 | 2230 | 1362 | 3393 | — | — | — | 72.22 (<0.0001) |

Consistent with the previous observations for *B. bassiana*, median lethal time (LT$_{50}$, time needed to kill 50% of nymphs) for aerial conidia was significantly longer (t=9.88, P<0.0001) than that calculated for blastospores, resulting in a significant increase in speed of kill (>37% faster) by blastospores (Table 10). Ten insects per treatment (2.0×10$^4$ spores/cm$^2$) were tested and control insects were sprayed with Tween 80 solution at 0.01%. Mortality averaged 11.5±1.6% after 6 days. Blastospores of *I. fumosorosea* required 70% fewer spores to incite 50% mortality as well as faster mortality of nymphs (t=2.52, P=0.0215) when compared with conidia. The majority of nymphal cadavers infected by both types of propagules supported fungal outgrowth that subsequently sporulated.

TABLE 10

B. bassiana (ESALQ1423) blastospores kill whiteflies quicker than conidia

| Fungus | Propagule type | $n^a$ | Median survival time (days)$^b$ | 95% CL (days) Lower | Upper |
|---|---|---|---|---|---|
| B. bassiana | Blastospores | 512 | 2.45 ± 0.05 b | 2.34 | 2.55 |
| | Conidia | 561 | 3.35 ± 0.07 a | 3.21 | 3.49 |

Figure 12:
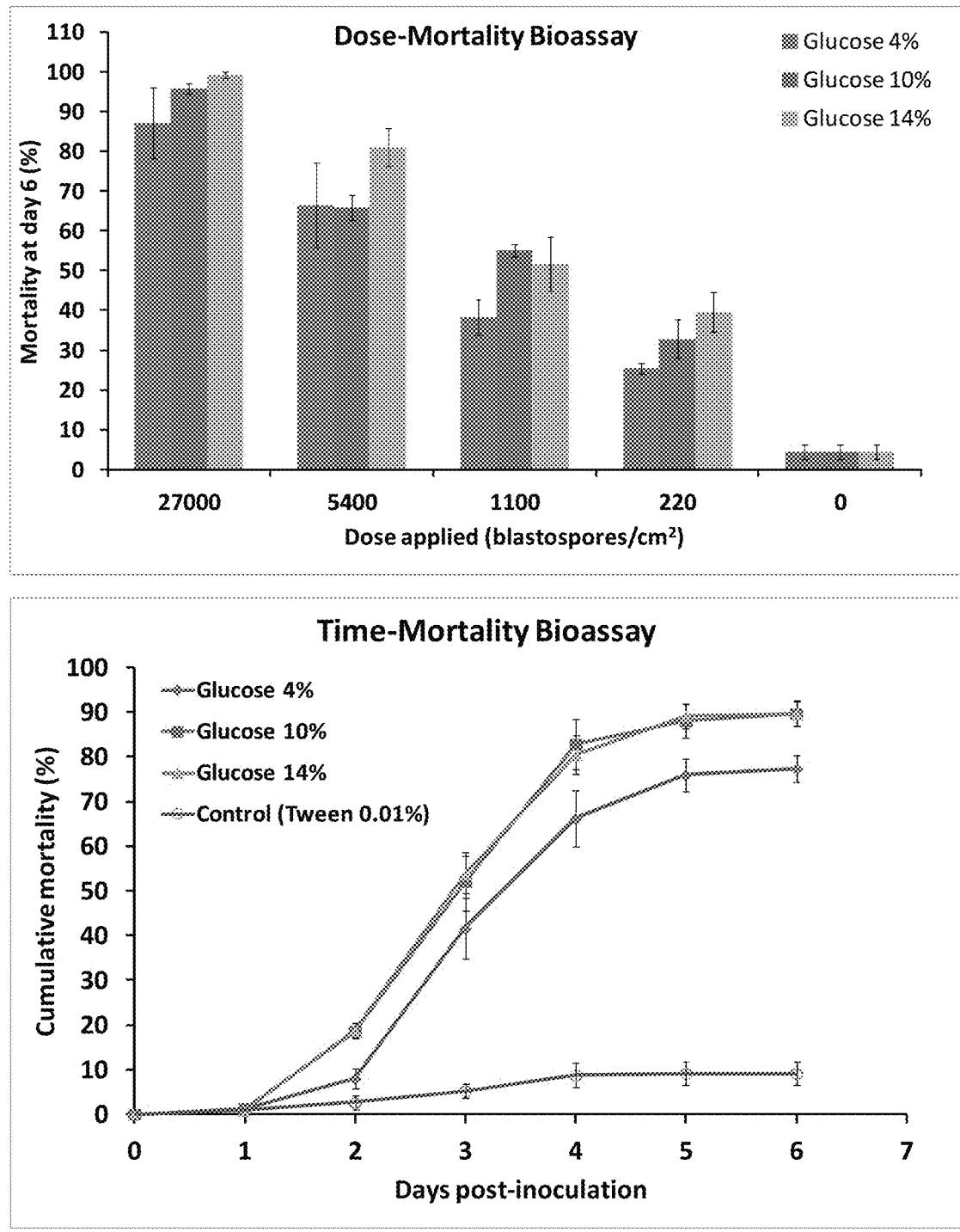
FIG. 12 provides two panels demonstrating the effects of blastospores grown in high osmotic pressure cultures on entomopathogenic effectiveness.

To examine whether blastospores grown under high osmotic pressure showed good effectivity against whitefly nymphs, blastospores of *B. bassiana* (ESALQ1432) were produced in a liquid medium with fixed amount (2.5%) of cottonseed flour and glucose at 4%, 10%, and 14% glucose after 3 days growth. Blastospores were separated from the culture broth with diatomaceous earth and air-dried, or encapsulated in a skim milk matrix (SMP) and spray dried. The results shown in FIG. 12 indicate that the smaller, rounded cells produced under high osmotic pressure (10% and 14% glucose) showed increased infectiveness and killed the insects more quickly.

What is claimed is:

1. An insecticidal composition, comprising an agronomically acceptable carrier and desiccation-tolerant blastospores of *Beauveria bassiana* with greater than 60% germination when rehydrated and grown in a suitable medium after storage for more than six months at 4° C., wherein said carrier and said blastospores are contained in air-tight packaging and wherein said blastospores are produced by a method comprising the steps of:
    a) inoculating a liquid culture medium comprising a carbon source and a nitrogen source with fungal propagules of *Beauveria basianna*, wherein said nitrogen source is present in said liquid culture medium at an initial concentration of at least 1.5% (w/v);
    b) incubating said propagules under liquid culture conditions providing dissolved oxygen levels above zero and osmotic pressure greater than 0.5 MPa;
    c) incubating said propagules in said liquid culture for a sufficient time to produce blastospores;
    d) collecting said blastospores; and
    e) drying said blastospores, thereby producing desiccation-tolerant blastospores.

2. The composition of claim 1, further comprising an oxygen scavenging compound, a moisture scavenging compound, or a combination of both.

3. The composition of claim 1, wherein said method further comprises the step of storing the blastospores at a temperature of 4° C. or lower.

4. A method for insect control comprising applying to the site of said insects an insecticidally effective amount of the composition of claim 1.

5. The method of claim 4, wherein said carbon source is glucose and said nitrogen source is cottonseed flour or hydrolyzed casein.

6. The method of claim 4, wherein said site is an agricultural crop.

7. A method of producing a composition, wherein said composition comprises desiccation-tolerant blastospores of *Beauveria bassiana* with greater than 60% germination when rehydrated and grown in a suitable medium after storage for more than six months at 4° C., comprising the steps of:
    a) inoculating a liquid culture medium comprising a carbon source and a nitrogen source with fungal propagules of *Beauveria bassiana*, wherein said nitrogen source is present in said liquid culture medium at an initial concentration of at least 1.5% (w/v);
    b) incubating said propagules under liquid culture conditions providing dissolved oxygen levels above zero and osmotic pressure greater than 0.5 MPa;
    c) incubating said propagules in said liquid culture for a sufficient time to produce blastospores;
    d) collecting said blastospores; and
    e) drying said blastospores, thereby producing desiccation-tolerant blastospores.

8. The method of claim 7, wherein said carbon source is present in said liquid culture medium at an initial concentration of at least 4% (w/v).

9. The method of claim 8, wherein said carbon source is glucose.

10. The method of claim 7, wherein said nitrogen source is cottonseed flour or hydrolyzed casein.

11. The method of claim 7, wherein in said carbon source is glucose and said nitrogen source is cottonseed flour.

* * * * *